United States Patent [19]

Civelli et al.

[11] Patent Number: 5,686,573
[45] Date of Patent: Nov. 11, 1997

[54] HUMAN D5 DOPAMINE RECEPTOR PROTEIN

[75] Inventors: Olivier Civelli; David K. Grandy, both of Portland, Oreg.

[73] Assignee: State of Oregon, Acting by and Through the Oregon State Board of Higher Education on Behalf of the Oregon Health Sciences University, a non-profit organization, Portland, Oreg.

[21] Appl. No.: 383,781

[22] Filed: Feb. 6, 1995

Related U.S. Application Data

[62] Division of Ser. No. 791,936, Nov. 13, 1991, Pat. No. 5,427,942.
[51] Int. Cl.$^6$ ................................................. C07K 14/705
[52] U.S. Cl. ........................ 530/350; 435/69.1; 530/395; 536/23.5
[58] Field of Search ..................... 530/350, 395; 435/69.1; 536/23.5

[56] References Cited

PUBLICATIONS

Grandy et al., *P.N.A.S.* 88:9175–9179, Oct. 1991.
Sunahara et al., *Nature* 350:614–619, 18 Apr. 1991.

*Primary Examiner*—John Ulm
*Attorney, Agent, or Firm*—Banner & Allegretti, Ltd.

[57] ABSTRACT

The present invention relates to the isolation, characterization and pharmacological uses for the human D5 dopamine receptor, the gene corresponding to this receptor, pseudogenes of this receptor gene, a recombinant eukaryotic expression vector capable of expressing the human D5 dopamine receptor in cultures of transformed eukaryotic cells and such cultures of transformed eukaryotic cells that synthesize the human D5 dopamine receptor. The invention relates to the biochemical and physiological characterization of the human D5 dopamine receptor and the development and testing of drugs useful for treating or preventing human disease.

1 Claim, 18 Drawing Sheets

FIG. 2A

```
       -147 CCCGGCGCAGCTCATGGTGAGCGCCGCCTCTGGGGTCTGCTCGAGGGTCC
            CTTGGCTGAGGGGGCGCATCCTCGGGGTGCCCCTGCCCTGGGGGTC
            GCAGGGCTGAAGTTGGGATCGCGCACAAACCGACCCTCCAGTCCCGAA
                                         *
            Met Leu Pro Pro Gly Ser Asn Gly Thr Ala
                                                  10
hD5         ATG CTG CCG CCA GGC AGC AAC GGC ACC GCG
hD5 Ψ1                      A   A
hD5 Ψ2                      G   G                 30

Tyr Pro Gly Gln Phe Ala Leu Tyr Gln Gln
                                              20
hD5         TAC CCG GGG CAG TTC GCT CTA TAC CAG CAG
hD5 Ψ1                          G
hD5 Ψ2                          G                 60

Leu Ala Gln Gly Asn Ala Val Gly Gly Ser
                                              30
hD5         CTG GCG CAG GGG AAC GCC GTG GGG GGC TCG
hD5 Ψ1                  A
hD5 Ψ2                  A                         90

Ala Gly Ala Pro Pro Leu Gly Pro Ser Gln
                                              40
hD5         GCG GGG GCA CCG CCA CTG GGG CCC TCA CAG
hD5 Ψ1              T
hD5 Ψ2                                            120
                                                  GTG
                                                  GTG
```

FIG. 2B

```
              Val  Val  Thr  Ala  Cys  Leu  Leu  Thr  Leu  Leu                50
      h D5    GTG  GTC  ACC  GCC  TGC  CTG  CTG  ACC  CTA  CTC               150
      h D5 Ψ1
      h D5 Ψ2

Ile  Ile  Trp  Thr  Leu  Leu  Leu  Gly  Asn  Val  Leu           60
      h D5    ATC  ATC  TGG  ACC  CTG  CTG  CTG  GGC  AAC  GTG  CTG          180
      h D5 Ψ1                I                  T
      h D5 Ψ2                                   T

Val  Cys  Ala  Ala  Ile  Val  Arg  Ser  Arg  His               70
      h D5    GTG  TGC  GCA  GCC  ATC  GTG  CGG  AGC  CGC  CAC               210
      h D5 Ψ1  A          C       *
      h D5 Ψ2             C

Leu  Arg  Ala  Asn  MET  Thr  Asn  Val  Phe  Ile               80
      h D5    CTG  CGC  GCC  AAC  ATG  ACC  AAC  GTC  TTC  ATC               240
      h D5 Ψ1            G
      h D5 Ψ2            G
```

FIG. 2C

```
                                                                    II              90
         Val Ser Leu Ala Val Ser Asp Leu Phe Val
hD5      GTG TCT CTG GCC GTG TCT GAC CTT TTC GTG                                   270
hD5 Ψ1            T              A              C
hD5 Ψ2         A  C  T           A              C

100
         Ala Leu Leu Val MET Pro Trp Lys Ala Val
hD5      GCG CTG CTG GTC ATG CCC TGG AAG GCA GTC                                   300
hD5 Ψ1
hD5 Ψ2

110
         Ala Glu Val Ala Gly Tyr Trp Pro Phe Gly
hD5      GCC GAG GTG GCC GGT TAC TGG CCC TTT GGA                                   330
hD5 Ψ1                            T                                                  A
hD5 Ψ2

120
         Ala Phe Cys Asp Val Trp Val Ala Phe Asp
hD5      GCG TTC TGC GAC GTC TGG GTG GCC TTC GAC                                   360
hD5 Ψ1
hD5 Ψ2
```

FIG. 2D

```
                     III                                                              130
              Ile MET Cys Ser Thr Ala Ser Ile Leu Asn
hD5           ATC ATG TGC TCC ACT GCC TCC ATC CTG AAC         390
hD5 Ψ1                        C
hD5 Ψ2                        C

140
              Leu Cys Val Ile Ser Val Asp Arg Tyr Trp
hD5           CTG TGC GTC ATC AGC GTG GAC CGC TAC TGG         420
hD5 Ψ1                    GCAGGTCA    G
hD5 Ψ2                    GCAGGTCA    C

150
              Ala Ile Ser Arg Pro Phe Arg Tyr Lys Arg
hD5           GCC ATC AGC AGG CCC TTC CGC TAC AAG CGC         450
hD5 Ψ1                                            G
hD5 Ψ2                                            G

160
              Lys MET Thr Gln Arg MET Ala Leu Val MET
hD5           AAG ATG ACT CAG CGC ATG GCC TTG GTC ATG         480
hD5 Ψ1                 C
hD5 Ψ2                 C
```

FIG. 2E

```
             Val Gly Leu Ala Trp Thr Leu Ser Ile  170
                                                  Leu
hD5          GTC GGC CTG GCA TGG ACC TTG TCC ATC  CTC  510
hD5 Ψ1               C   C               G
hD5 Ψ2               C   C               G
                  IV
             Ile Ser Phe Ile Pro Val Gln Leu Asn  180
                                                  Trp
hD5          ATC TCC TTC ATT CCG GTC CAG CTC AAC  TGG  540
hD5 Ψ1
hD5 Ψ2

His Arg Asp Gln Ala Ser Trp Gly      190
                                             Gly
hD5          CAC AGG GAC CAG GCG TCT TGG GGC  GGG  570
hD5 Ψ1                            T   A
hD5 Ψ2                            T   A

Leu Asp Leu Pro Asn Asn Leu Ala Asn  200
                                                  Trp
hD5          CTG GAC CTG CCA AAC AAC CTG GCC AAC  TGG  600
hD5 Ψ1                                    *
hD5 Ψ2
```

FIG. 2F

```
                                                        210                     Pro
         Thr Pro Trp Glu Glu Asp Phe Trp Glu            Pro                     CCC
hD5      ACG CCC TGG GAG GAG GAC TTT TGG GAG            CCC                     630
hD5 Ψ1                               G                                           T
hD5 Ψ2                               G

220
         Asp Val Asn Ala Glu Asn Cys Asp Ser                                     Ser
hD5      GAC GTG AAT GCA GAG AAC TGT GAC TCC                                     AGC
hD5 Ψ1           GG                                                              660
hD5 Ψ2           GG
              *

230
         Leu Asn Arg |Thr Tyr Ala Ile Ser Ser           Ser|                     Ser
hD5      CTG AAT CGA |ACC TAC GCC ATC TCT TCC           TCC|                     TCG
hD5 Ψ1       A                                                                   690
hD5 Ψ2                     v

240
         |Leu Ile Ser Phe Tyr Ile Pro Val Ala           Ile|
hD5      |CTC ATC AGC TTC TAC ATC CCC GTT GCC           ATC|
hD5 Ψ1                                  A                                        720
hD5 Ψ2                                  A   G
```

FIG. 2G

```
       MET  Ile  Val  Thr  Tyr  Thr  Arg  Ile  Tyr  Arg
                                                    250
hD5    ATG  ATC  GTG  ACC  TAC  ACG  CGC  ATC  TAC  CGC
Ψ1                                                      
Ψ2                                                   750

Ile  Ala  Gln  Val  Gln  Ile  Arg  Arg  Ile  Ser
                                                    260
hD5    ATC  GCC  CAG  GTG  CAG  ATC  CGC  AGG  ATT  TCC
Ψ1                                    T                 
Ψ2                                                   780

Ser  Leu  Glu  Arg  Ala  Ala  Glu  His  Ala  Gln
                                                    270
hD5    TCC  CTG  GAG  AGG  GCC  GCA  GAG  CAC  GCG  CAG
Ψ1      T                                         T     
Ψ2                                                T  810

Ser  Cys  Arg  Ser  Ser  Ala  Ala  Cys  Ala  Pro
                                                    280
hD5    AGC  TGC  CGG  AGC  AGC  GCA  GCC  TGC  GCG  CCC
Ψ1                                    G           A     
Ψ2                                    G                840
```

FIG. 2H

```
                                                                    290              300
      Asp Thr Ser Leu Arg Ala Ser Ile Lys    Glu Thr Lys Val Leu Lys Thr Leu Ser Val
hD5   GAC ACC AGC CTG CGC GCT TCC ATC AAG    GAG ACC AAG GTT CTC AAG ACC CTG TCG GTC
hΨ1                       G   TT                  G                       C       A
hΨ2                       G   TT                                                  
                                        870                                        900

310                                       320
      Ile MET Gly Val Phe Val Cys Cys Trp Leu    Pro Phe Phe Ile Leu Asn Cys MET Val Pro
hD5   ATC ATG GGG GTC TTC GTG TGT TGC TGG CTG    CCC TTC TTC ATC CTT AAC TGC ATG GTC CCT
hΨ1                                                                                
hΨ2                                       VI                                       
                                         930                                       960
```

FIG. 21

```
         Phe Cys Ser Gly His Pro Glu Gly Pro     330
hD5      TTC TGC AGT GGA CAC CCT GAA GGC CCT     Pro
hD5 Ψ1       C              C   A                CCG
hD5 Ψ2       C              C   A                990

Ala Gly Phe Pro Cys Val Ser Glu     340 Thr Thr
hD5      GCC GGC TTC CCC TGC GTC AGT GAG         ACC ACC
hD5 Ψ1         T                                      1020 A
hD5 Ψ2                                                     A

Phe Asp Val Phe Val Trp Phe Gly Trp Ala     VII 350
hD5      TTC GAC GTC TTC GTC TGG TTC GGC TGG GCT
hD5 Ψ1    *              A      T                         1050 C
hD5 Ψ2                   A      T                              C

Asn Ser Ser Leu Asn Pro Val Ile Tyr Ala         360
hD5      AAC TCC TCA CTC AAC CCC GTC ATC TAT GCC
hD5 Ψ1                         A              -          1080
hD5 Ψ2                         A              -
```

FIG. 2J

```
       Phe Asn Ala Asp Phe Gln Lys Val Phe Ala   370
hD5    TTC AAC GCC GAC TTT CAG AAG GTG TTT GCC  1110
hD5 Ψ1                  C  TG
hD5 Ψ2                  C  G

Gln Leu Leu Gly Cys Ser His Phe Cys Ser   380
hD5    CAG CTG CTC GGG TGC AGC CAC TTC TGC TCC  1140
hD5 Ψ1                                  G
hD5 Ψ2                                  G

Arg Thr Pro Val Glu Thr Val Asn Ile Ser   390
hD5    CGC ACG CCG GTG GAG ACG GTG AAC ATC AGC  1170
hD5 Ψ1             *
hD5 Ψ2

Asn Glu Leu Ile Ser Tyr Asn Gln Asp Ile   400
hD5    AAT GAG CTC ATC TCC TAC AAC CAA GAC ATC  1200
hD5 Ψ1                                       G
hD5 Ψ2                                       CG
```

FIG. 2K

```
       Val Phe Hes Lus Glu Ile Ala Ala Tyr
                              410
hD5    GTC TTC CAC AAG GAA ATC GCA GCT TAC
hD5 Ψ1                                    1230
hD5 Ψ2                                    G

Ile Hes MET MET Pro Asn Ala Val Thr Pro
                              420
hD5    ATC CAC ATG ATG CCC AAC GCC GTT ACC CCC
hD5 Ψ1         G                              1260
hD5 Ψ2         G                      C

Gly Asn Arg Glu Val Asp Asn Asp Glu Glu
                              430
hD5    GCC AAC CGG GAG GTG GAC AAC GAC GAG GAG
hD5 Ψ1     G   AA                             1290
hD5 Ψ2     G                      T   T

Glu Gly Pro Phe Asp Arg MET Phe Gln Ile
                              440
hD5    GAG GGT CCT TTC GAT CGC ATG TTC CAG ATC
hD5 Ψ1 AGG A                                  1320
hD5 Ψ2 AGG A                          C   C
```

FIG. 2L

```
           Tyr Gln Thr Ser Pro Asp Gly Asp Pro Val  450
hD5        TAT CAG ACG TCC CCA GAT GGT GAC CCT GTT  1350
hΨ1                    A       A
hΨ2                    A       A

Ala Glu Ser Val Trp Glu Leu Asp Cys Glu  460
hD5        GCT GAG TCT GTC TGG GAG CTG GAC TGC GAG  1380
hΨ1            A                   A
hΨ2            A                   A

Gly Glu Ile Ser Leu Asp Lys Ile Thr Pro  470
hD5        GGG GAG ATT TCT TTA GAC AAA ATA ACA CCT  1410
hΨ1                                            G
hΨ2                            G

477
           Phe Thr Pro Asn Gly Phe His
hD5        TTC ACC CCG AAT GGA TTC CAT TAAACTGCATT  1442
hΨ1            A       A
hΨ2            A       A hD5   AAGAAACCCCTCATGGATCTGCATAACCGCACAGACACTGACA
hΨ1
hΨ2   AGCACGCACACATGCAAATACATGCCTTTCCAGTACTG 1526
```

FIG. 3A

```
                                                                                            I
HUMAN.D5......       .......MLPPGSNGTAYPGQFALYQQLAQGNAVGGSAGAPPLGPSQVVTACLLTLLIIWTLL.GNVLVCAAIVRSRH
HUMAN.D1......       ..............................MRTLNTSAMDGTGLVVERDFSVRILTACFLSLILSTLL.GNTLVCAAVIRFRH
HUMAN.D2......       .....................MDPLNLSWYDDDLERQNWSRPFNGSDGKADRPHYNY...ATLLTLLIAVIVF.GNVLVCMAVSREKA
HUMAN.D3......       .............................MASLSQLSSHLNYTCGAENSTGASQARPHAYY......ALSYCALILAIVF.GNGLVQMAVLKERA
HUMAN.D4......       MGNRSTADADGLLAGRGPAAGASA......GASAGLAGQGAA....ALVGGVLLIGAVLAGNSLVQVSVATERA

III
HUMAN.D5......       .LRANMTNVPIVSLAVSDIFVALLVMPWKAVAEVAGY.WPFGAF..CDVWVAFDIM.CSTASILNICVIGVPRYM
HUMAN.D1......       .LRSKVTNFFVISLAVSDLLVAVLVMPWKAVAEIIAGF.WPFGSF..CNIWVAFDIM.CSTASILNLCVISVDRYW
HUMAN.D2......       .LQTT.TNYLIVSLAVADLLVATLVMPWVVYLEVVGE.WKFSRIH.CDIFVTLDVMMC.TASILNLCAISIDRYT
HUMAN.D3......       .LQT..TTNYLVVSLAVADLLVATLVMPWVVYLEVTGGWNFSRIC..CDVFVTLDVMMC.TASILNLCATSIDRYT
HUMAN.D4......       .LQT..PTNSFIVSLAAADILLALLVLPLFVYSEVQGGAWLLSPR.LCDALMAMDVMLC.TASIFNLCAISVDRFV

IV
HUMAN.D5......       .AISRPFRYKRKMTQRM...ALVMVGLA.WTLSILTSFIPVQLNWHRDQAASWGGLDLPNNLANWTPWEEDFWEP..
HUMAN.D1......       .AISSPFRYERKMTPKA..AFILISVA.WTLSVLISFIPVQLSWHKAKPTSPSDGNATSLAETID........
HUMAN.D2......       .AVAMPMLYNTRYSSKRRVTVMISIV..WVLSFTISC.PLLFGLNNADQ..................
HUMAN.D3......       .AVVMPVHYQHGTGQSSCRRVALMIT.AVWVLAFAVSC.PLLFGFNTTGDPT.................
HUMAN.D4......       .AVAVPLRYNRQGGSRR..QLLLIG.ATWLLSAAVAA.PVLCGLNDVRGRDP................
```

FIG. 3B

```
                                                                                                V
HUMAN.D5.....DVNAEN..CDSSLNRTYAISSSLISFYIPVATMIVTYTRIY....RIAQVQI..RRISSLERAAEHAQSCR.........
HUMAN.D1..........N..CDSSLSRTYAISSVISFYIPVAIMIVTYTRIY....RIAQKQI..RRIAALERAAVHAKNCQ......(8)
HUMAN.D2..........NECIANPAFVVYSSIV.SFYVPFIVTLLVYIKIYIVIR.......RRRKRVNTKRSSRAFRAH(115)
HUMAN.D3.......VCSISNPDFVIYSSVV.SFYLPFGVTVLVYARIYVLKQRRRKRILTRQNSQCNSVRPGFPQQ..(64)
HUMAN.D4.......AVCRLEDRDYVVYSSVC.SFFLPCPLMLLLYWATF...RGLQRWEVARRAKLHGRAPRRPSGPG..(56)

VI
HUMAN.D5......SSAACAPDTSLRASI..KKETKVLKTLSVIM......GVFVCCWLPFFILNCMVPFCSGHPEGPPAGFPC.VSE
HUMAN.D1......VECSQ..PESSFKMSF..KRETKVLKTLSVIM......GVFVCCWLPFFILNCIIPFCGSGETQPF....C.IDS
HUMAN.D2......TRTSLKTMSRRKLSQQ.KEKKATQMLAIVL......GVFIICWLPFFITHILNIHCD.........CNIPP
HUMAN.D3......LSTSLKLGPLQPRGVPLREKKATQMVAIVL......GAFIVCWLPFFLTHVLNTHCQT........CHVSP
HUMAN.D4........RRRRA..KITGRERKAMRVLPVVVGAFLLCWTPFFVVHITQALCPA..........CSVPP

VII
HUMAN.D5......TTFDVFVWFGWANSSLNPVIYA.FNADFQKVFAQLLG.CSHFICSRTPVETVNISNELISYNQDIVFHK...477
HUMAN.D1......NTFDVFVWFGWANSSLNPIIYA.FNADFRKAFSTLLG.CYRLCPATNNAIETVSINNGAAMFSSHHE...446
HUMAN.D2L......VLYSAFTWLGYVNSAVNPIIYTTFNIEFRKAFLKILH.C......443
HUMAN.D3......ELYSATTWLGYVNSALNPVIYTTFNIEFRKAFLKILS.C......400
HUMAN.D4......RLVSAVTWLGYVNSALNPVIYTVFNAEFRNVFRKALRACC...387
```

HUMAN D5 DOPAMINE RECEPTOR PROTEIN

This is a divisional of application Ser. No. 07/791,936 filed Nov. 13, 1991, now U.S. Pat. No. 5,427,942.

BACKGROUND OF THE INVENTION

This invention was made with government support under MH45614 by the National Institute of Mental Health. The government has certain rights in the invention.

FIELD OF THE INVENTION

This invention relates to dopamine receptors from mammalian species and the genes corresponding to such receptors. In particular, it relates to the human dopamine receptor D5. Specifically, the invention relates to the isolation, cloning and sequencing of the human D5 receptor gene. The invention also relates to pseudogenes of the human D5 receptor gene, and to the isolation, cloning, sequencing and characterization of such pseudogenes. Specifically, the present invention also relates to two pseudogenes of the human D5 dopamine receptor, D5ψ1 and D5ψ2. The invention also relates to the construction of eukaryotic expression vectors capable of expressing the human D5 dopamine receptor in cultures of transformed eukaryotic cells and the synthesis of the human D5 dopamine receptor in such cultures. The invention relates to the use of such cultures of transformed eukaryotic cells producing the human D5 dopamine receptor for the biochemical and physiological characterization of the human D5 dopamine receptor and the development and testing of drugs useful for treating or preventing human disease.

INFORMATION DISCLOSURE STATEMENT

Dopamine is a neurotransmitter that participates in a variety of different functions mediated by the nervous system, including vision, movement, and behavior. See generally Cooper et al., The Biochemical Basis of Neuropharmacology, (Oxford University Press, NY 3d Ed. 1978), pp. 161–195. Dopamine is an important transmitter molecule at the synapses of neurons in the mesocortico-mesolimbic, nigrostriatal and tuberinfundibular pathways of the brain. To a lesser extent, dopamine is also thought to be involved in the signaling between some hippocampal neurons. The central dopaminergic tracts in the brain have been of considerable medical interest due to their association with several psychiatric and neurological disorders including psychosis, compulsive behavior, drug abuse and Parkinson's disease.

The diverse physiological actions of dopamine are in turn mediated by its interaction with specific receptors. The majority of dopamine receptors are concentrated in the mesocortico-mesolimbic, nigrostriatal and tuberinfundibular pathways. These neuronal circuits are known to influence mood, behavior, initiation of movement and prolactin secretion. The dopamine receptors are integral membrane proteins which interact with G proteins to transduce dopamine stimulation into intracellular responses. Dopamine is thought to evoke its physiological responses through the stimulation of at least two of the basic types of G protein-coupled receptors: D1 and D2, which respectively stimulate and inhibit the enzyme adenyl cyclase. Kebabian and Calne, 1979, Nature 277: 93–96. These receptors can be differentiated on the basis of their pharmacology, physiology and anatomical distribution. Alterations in the number or activity of these receptors may be a contributory factor in disease states such as Parkinson's disease (a movement disorder) and schizophrenia (a behavioral disorder).

A great deal of information has accumulated on the biochemistry of the D1 and D2 dopamine receptors, and methods have been developed to solubilize and purify these receptor proteins. See Senogles et al., 1986, Biochemistry 25: 749–753; Sengoles et al., 1988, J. Biol. Chem. 263: 18996–19002; Gingrich et al., 1988, Biochemistry 27: 3907–3912. The D1 dopamine receptor in several tissues appears to be a glycosylated membrane protein of about 72 kDa. Amlaiky et al., 1987, Mol. Pharmacol. 31: 129–134; Ninik et al., 1988, Biochemistry 27: 7594–7599. The D2 receptor has been suggested to have a higher molecular weight of about 90–150 kDa. Amlaiky and Caron, 1985, J. Biol. Chem. 260: 1983–1986; Amlaiky and Caron, 1986, J. Neurochem. 47: 196–204; Jarvie et al., 1988, Mol. Pharmacol. 34: 91–97. Much less is known about a recently discovered dopamine receptor, termed D3. Sokoloff et al., 1990, Nature 347: 146–151. Dopamine receptors are also primary targets in the clinical treatment of psychomotor disorders such as Parkinson's disease and affective disorders such as schizophrenia. Seeman et al., 1987, Neuropsychopharm. 1: 5–15; Seeman, 1987, Synapse 1: 152–333. The three different dopamine receptors (D1, D2, D3) have been cloned as a result of nucleotide sequence homology which exists between these receptor genes. Bunzow et al., 1988, Nature 336: 783–787; Grandy et al., 1989, Proc. Natl. Acad. Sci. U.S.A. 86: 9762–9766; Dal Toso et al., 1989, EMBO J. 8: 4025–4034; Zhou et al., 1990, Nature 346: 76–80; Sunahara et al., 1990, Nature 346: 80–83; Sokoloff et al., 1990, Nature 347: 146–151, Van Tol et al., 1991, Nature 350: 610–614.

We have cloned and sequenced another human dopamine receptor which we termed D4. Zhou et al., 1990, Nature 947: 76–80. This receptor, the gene encoding it, and methods for using the receptor and its gene are disclosed in copending U.S. patent application Ser. No. 07/626,618, which is hereby incorporated by reference. The present invention relates to the isolation and characterization of yet another novel human dopamine receptor which we term D5. The dopamine D5 receptor gene has high homology to the human dopamine D1 receptor gene. The pharmacological profile of this receptor resembles that of the D1 receptor but with 2 distinct differences: the human D5 receptor shows a 5-fold lower affinity for the antagonist (+) butaclamol and a 10-fold higher affinity for dopamine. Further, the D5 receptor is able to stimulate adenylyl cyclase activity at dopamine concentrations which are 30-fold lower than required by the D1 receptor when expressed in the same cell line. These properties suggest that the D5 dopamine receptor disclosed as this invention may prove useful in discovering new types of drugs for a variety of psychological, neurological and motor-control diseases.

DESCRIPTION OF THE DRAWINGS

FIGS. 2A through 2L. The structure of a genomic clone comprising the nucleotide and deduced amino acid sequences of the human D5 dopamine receptor gene [hD$_5$ (clone HGRI-4=SEQ ID No: I)] and 2 related pseudogenes [hD$_5$Ψ$_1$ (clone HGRI-6=SEQ ID No: 3) & hD$_5$Ψ$_2$ (clone HGRI-8=SEQ ID No: 4)]. Only the nucleotide sequence differences in the coding region are given for the pseudogenes, with dashes indicating deletions and an expanded caret indicating insertions. The in-frame stop codon present in the sequence of the two pseudogenes (TGA) is boxed with a solid triangle over it. The seven proposed transmembrane domains are shaded and numbered by Roman numerals. The putative N-glycosylation sites are indicated by asterisks; the protein kinase A phosphorylation sites are overlined; the protein king C sites are overlined with a dashed line. A solid box identifies the cysteine residue which may be the site of palmitoylation. The stop codon for the D5 receptor, TAA, is identified by a dot.

FIGS. 3A and 3B. Amino acid sequence alignment of 5 cloned human dopamine receptors. The single letter amino acid code is used. Shaded residues are common between D5 and at least one other dopamine receptor. The putative transmembrane domains are overlined and numbered with Roman numerals. The number of residues not shown in the figure are given within the parentheses.

SUMMARY OF THE INVENTION

Figure 1:
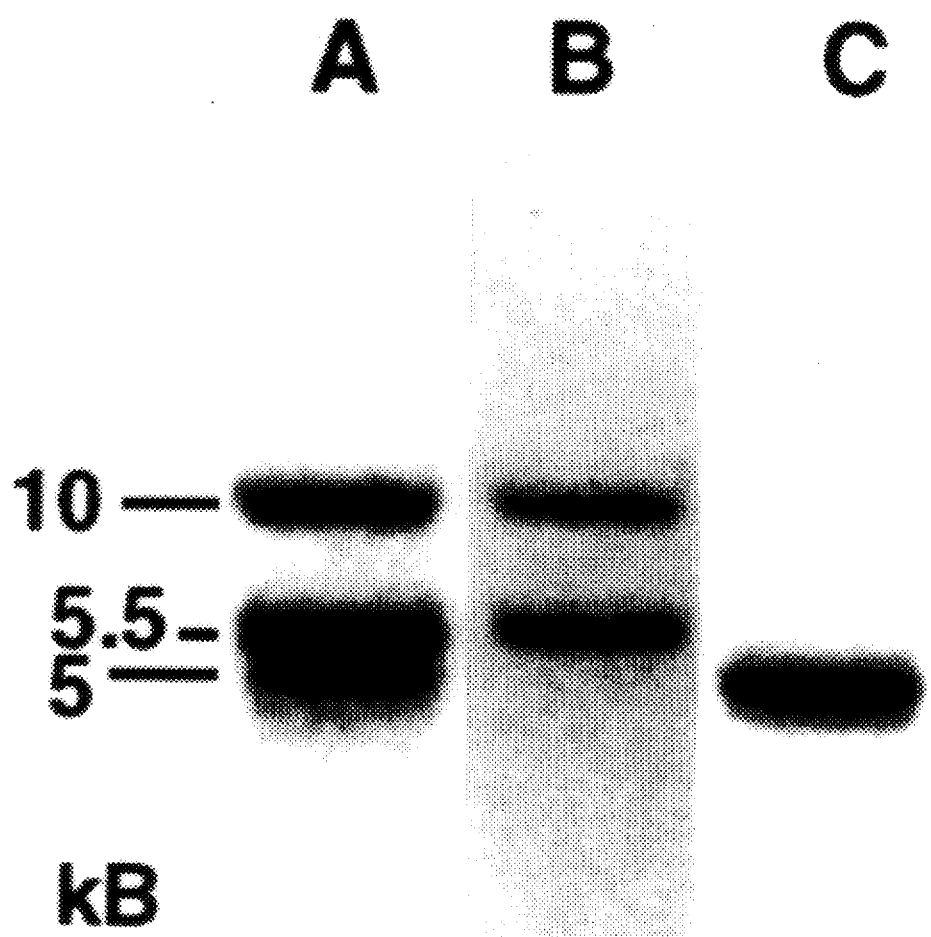
FIG. 1. Southern blot of human genomic DNA probed with a D1 gene probe at low stringency (Panel A) and high stringency (Panel B) and probed with a human D5 clone (Panel C).

The present invention relates to the isolation, characterization and pharmacological uses for the human D5 dopamine receptor, the gene corresponding to this receptor, pseudogenes of this receptor gene, a recombinant eukaryotic expression vector capable of expressing the human D5 dopamine receptor in cultures of transformed eukaryotic cells and such cultures of transformed eukaryotic cells that synthesize the human D5 dopamine receptor.

It is an object of the invention to provide a nucleotide sequence encoding a mammalian dopamine receptor. Further, it is an object of the invention to provide a nucleotide sequence that encodes a mammalian dopamine receptor with novel and distinct pharmacological properties. It is specifically an object of the invention to provide a nucleotide sequence encoding a mammalian dopamine receptor having the particular dopamine binding properties of the human dopamine receptor D5. In particular, the mammalian dopamine receptor encoded by the nucleotide sequence of the present invention has a high affinity for dopamine. In a preferred embodiment, the nucleotide sequence provided by the present invention encodes the D5 human dopamine receptor.

The invention includes a nucleotide sequence derived from human genomic DNA. The present invention provides the nucleotide sequence of the human D5 dopamine receptor, said sequence essentially homologous to the sequence represented in FIG. 2 (SEQ ID NO: 1). In this embodiment of the invention, the nucleotide sequence includes 5 kilobases (kb) of human genomic DNA encoding the dopamine receptor D5. This embodiment includes the sequences encoding the D5 dopamine receptor.

The present invention includes a nucleotide sequence encoding a mammalian dopamine receptor derived from a DNA molecule isolated from a human genomic DNA library constructed with DNA from human leukocytes. In a preferred embodiment, this DNA molecule is a recombinant bacteriophage termed HGRI-4. The present invention also provides the nucleotide sequence of the human genomic DNA comprising HGRI-4, said sequence essentially homologous to the sequence represented in FIG. 2 (SEQ ID NO: 1 ).

The invention includes a nucleotide sequence of a human D5 receptor molecule, and includes allelic variations of this nucleotide sequence and the corresponding D5 receptor molecule, either naturally occurring or the product of in vitro chemical or genetic modification, having essentially the same nucleotide sequence as the nucleotide sequence of the human D5 receptor disclosed herein, wherein the resulting human D5 receptor molecule has substantially the same drug and dopamine dissociation properties of the human D5 receptor molecule corresponding to the nucleotide sequence described herein.

The present invention also includes 2 related but distinct pseudogenes of the human D5 dopamine receptor gene. For purposes of this invention, the term pseudogene is meant to include transcriptionally and translationally inactive sequences, homologous to a corresponding functional gene from which these pseudogenes may have arisen, which can be distinguished from the cognate functional gene on the basis of mutational differences in the sequences, at least some of such mutational sequences differences would result in premature termination of translation due to the presence of codon sequences that signal translational termination. In a preferred embodiment, one of these pseudogenes is designated D5ψ1, and shares 95 % sequence homology with the cognate D5 dopamine receptor gene. In another preferred embodiment, one of these pseudogenes is designated D5ψ2, and shares 93% sequence homology with the cognate D5 dopamine receptor gene.

The present invention also includes nucleotide sequences encoding 2 related but distinct pseudogenes of a mammalian dopamine receptor derived from DNA molecules isolated from a human genomic DNA library constructed with DNA from human leukocytes. In a preferred embodiment, these DNA molecules are recombinant bacteriophage. In a preferred embodiment, the human D5ψ1 pseudogene-containing recombinant phage is termed HGRI-6. In another preferred embodiment, the human D5ψ2 pseudogene-containing recombinant phage is termed HGRI-8. The present invention also provides the nucleotide sequence of the human genomic DNA comprising HGRI-6, said sequence essentially homologous to the sequence represented in FIG. 2 (SEQ ID NO:2). The present invention also provides the nucleotide sequence of the human genomic DNA comprising HGRI-8, said sequence essentially homologous to the sequence represented in FIG. 2 (SEQ ID NO:3).

The present invention also includes nucleotide sequence encoding the human D5 dopamine receptor derived from a DNA molecule isolated from a human genomic DNA library constructed with DNA from human leukocytes and amplified in vitro using methods well known to those with skill in the art. In a preferred embodiment, the sequences are amplified by polymerase chain reaction. In this embodiment of the invention, the nucleotide sequence includes 1434 nucleotides of the human D5 dopamine receptor gene comprising transmembrane domains I–VII.

The present invention also includes nucleotide sequences encoding 2 related but distinct pseudogenes of a mammalian dopamine receptor derived from DNA molecules isolated from a human genomic DNA library constructed with DNA from human leukocytes and amplified in vitro. In a preferred embodiment, the sequences are amplified by polymerase chain reaction.

The invention also includes a predicted amino acid sequence for the human D5 dopamine receptor deduced from the nucleotide sequence comprising the complete coding sequence of the D5 dopamine receptor gene.

This invention provides both nucleotide and amino acid probes derived from these sequences. The invention includes probes isolated from either the functional D5 receptor sequences or either of its related but distinct pseudogenes, or the DNA clones of these genes, as well as probes made synthetically with the sequence information derived therefrom. The invention specifically includes but is not limited to oligonucleotide, nick-translated, random primed, or in vitro amplified probes made using cDNA or genomic clones embodying the invention, and oligonucleotide and other synthetic probes synthesized chemically using the nucleotide sequence information of the different embodiments of the invention.

It is a further object of this invention to provide sequences of the human D5 dopamine receptor for use as a probe to determine the pattern, amount and extent of expression of this receptor in various tissues of mammals, including humans.

It is also an object of the present invention to provide probes derived from the sequences of the human D5 dopamine receptor to be used for the detection and diagnosis of genetic diseases.

It is an object of this invention to provide probes derived from the sequences of the human D5 dopamine receptor to be used for the detection of novel related receptor genes.

The present invention also includes synthetic peptides made using the nucleotide sequence information comprising the embodiments of the invention. The invention includes either naturally occurring or synthetic peptides which may be used as antigens for the production of D5 dopamine receptor-specific antibodies, or used for competitors of the D5 receptor molecule for drug binding, or to be used for the production of inhibitors of the binding of dopamine or dopamine analogs of the D5 dopamine receptor molecule.

In addition, this invention includes a cloning vector comprising the human D5 dopamine receptor and sequences that mediate the replication and selected growth of microorganisms that carry this vector.

The present invention provides a recombinant expression vector comprising the nucleotide sequence of the human D5 dopamine receptor and sequences sufficient to direct the synthesis of human D5 dopamine receptor in cultures of transformed eukaryotic cells. In a preferred embodiment, the recombinant expression vector is comprised of plasmid sequences derived from the plasmid pBC12 B1 and human D5 dopamine receptor sequences derived from the recombinant phage HGRI-4 by in vitro amplification of the sequences encoding the receptor. This invention includes a recombinant expression vector comprising essentially the nucleotide sequences of genomic clones of the human D5 dopamine receptor in an embodiment that provides for their expression in cultures of transformed eukaryotic cells.

In addition, this invention includes a cloning vector comprising the 2 related but distinct pseudogenes of the human D5 dopamine receptor and sequences that mediate the replication and selected growth of microorganisms that carry this vector.

The present invention provides a recombinant expression vector comprising the nucleotide sequence of the 2 related but distinct pseudogenes of the human D5 dopamine receptor and sequences sufficient to direct the synthesis of truncated human D5 dopamine receptor-related proteins in cultures of transformed eukaryotic cells. In a preferred embodiment, the recombinant expression vector is comprised of plasmid sequences derived from the plasmid pBC12 B1 and human D5 dopamine receptor pseudogene D5ψ1 sequences derived from the recombinant phage HGRI-6 by in vitro amplification of the sequences encoding the receptor. In another preferred embodiment, the recombinant expression vector is comprised of plasmid sequences derived from the plasmid pBC12 B1 and human D5 dopamine receptor pseudogene D5ψ2 sequences derived from the recombinant phage HGRI-8 by in vitro amplification of the sequences encoding the receptor. This invention includes a recombinant expression vector comprising essentially the nucleotide sequences of genomic clones of the human D5 dopamine receptor pseudogenes in an embodiment that provides for their expression in cultures of transformed eukaryotic cells.

It is also an object of this invention to provide cultures of transformed eukaryotic cells that have been transformed with such a recombinant expression vectors and that synthesize human D5 dopamine receptor protein or truncated proteins related thereto. In a preferred embodiment, the invention provides monkey COS cells that synthesize human D5 dopamine receptor protein or truncated proteins related thereto.

The present invention also includes protein preparations of the human D5 dopamine receptor or truncated proteins related thereto, and preparations of membranes containing the human D5 dopamine receptor or truncated proteins related thereto, derived from cultures of transformed eukaryotic cells. In a preferred embodiment, cell membranes containing human D5 dopamine receptor protein is isolated from culture of COS-7 cells transformed with a recombinant expression vector that directs the synthesis of human D5 dopamine receptor. In additional preferred embodiments, cell membranes containing truncated protein products of human D5 dopamine receptor pseudogenes D5ψ1 or D5ψ2 are isolated from culture of COS-7 cells transformed with a recombinant expression Vector that directs the synthesis of human D5 dopamine receptor.

The human D5 dopamine receptor embodied in the present invention is capable of binding a variety of dopamine agonists and antagonists, and to be characterized by the biochemical dissociation constant (termed $K_d$) for such dopamine agonists and antagonists. In a preferred embodiment, the human D5 dopamine receptor provided by the present invention displays a $K_d$ =0.35 nanomolar (nM) towards the dopamine antagonist SCH23390, as detected by the binding assay disclosed herein. The human D5 dopamine receptor embodied in the present invention displays the following pharmacological profile of inhibition of [$^3$H] spiperone binding in a [$^3$H]spiperone binding assay: SCH23390>(+)-butaclamol>cis-flupenthixol>haloperidol >clozapine.>>(−)-butaclamol.

It also an object of this invention to provide the human D5 dopamine receptor for use in the in vitro screening of novel compounds for the prevention, treatment, and alleviation of dopamine-related disease. In a preferred embodiment, membrane preparations containing the human D5 dopamine receptor, derived from cultures of transformed eukaryotic cells, are used to determine the drug dissociation properties of such compounds in vitro. These properties may then be used to characterize novel compounds by comparison to the binding properties of known dopamine agonists and antagonists.

The present invention will also be useful for the in vivo detection of dopamine and dopamine analogues, known or unknown, either naturally occurring or as the embodiments of antipsychotic or other drugs.

It is an object of the present invention to provide a method for the quantitative detection of dopamine and a dopamine analog, either naturally occurring or as the embodiments of antipsychotic or other drugs. It is an additional object of the invention to provide a method to detect dopamine or a dopamine analog in blood, saliva, semen, cerebrospinal fluid, plasma, lymph, or any other bodily fluid.

DETAILED DESCRIPTION OF THE PREFERRED EMBODIMENTS

The term "D5-dopamine receptor" as used herein refers to proteins substantially homologous to, and having substantially the same biological activity as, the protein coded for by the nucleotide sequence depicted in FIG. 2 (i.e., proteins which display high affinity binding to dopamine). This definition is intended to encompass natural allelic variations in the D5-dopamine receptor sequence. Cloned genes of the present invention may code for D5-dopamine receptors of any species of origin, including, mouse, rat, rabbit, cat, and human, but preferably code for receptors of mammalian, most preferably human, origin.

The production of proteins such as the D5-dopamine receptor from cloned genes by genetic engineering is well known. See, e.g., U.S. Pat. No. 4,761,371 to Bell et al. at Col. 6 line 3 to Col. 9 line 65. (The disclosure of all U.S. patent references cited herein is to be incorporated herein by reference.) The discussion which follows is accordingly intended as an overview of this field, and is not intended to reflect the full state of the art.

DNA which encodes the D5-dopamine receptor may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of MRNA or genomic DNA may be carried out with oligonucleotide probes generated from the D5-dopamine receptor gene sequence information provided herein. Probes may be labeled with a detectable group such as a fluorescent group, a radioactive atom or a chemiluminescent group in accordance with know procedures and used in conventional hybridization assays, as described in greater detail in the Examples below. In the alternative, D5-dopamine receptor gene sequences may be obtained by use of the polymerase chain reaction (PCR) procedure, with the PCR oligonucleotide primers being produced from the D5-dopamine receptor gene sequence provided herein. See U.S. Pat. Nos. 4,683,19:5 to Mullis et al. and 4,683,202 to Mullis.

The D5-dopamine receptor may be synthesized in host cells transformed with vectors containing DNA encoding the D5-dopamine receptor. A vector is a replicable DNA construct. Vectors are used herein either to amplify DNA encoding the D5-dopamine receptor and/or to express DNA which encodes the D5-dopamine receptor. An expression vector is a replicable DNA construct in which a DNA sequence encoding the D5 receptor is operably linked to suitable control sequences capable of effecting the expression of the D5 receptor in a suitable host. The need for such control sequences will vary depending upon the host selected and the transformation method chosen. Generally, control sequences include a transcriptional promoter, an optional operator sequence to control transcription, a sequence encoding suitable MRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integrable DNA fragments (i.e., fragments integrable into the host genome by homologous recombination). The vector replicates and functions independently of the host genome, or may, in some instances, integrate into the genome itself. Suitable vectors will contain replicon and control sequences which are derived from species compatible with the intended expression host. Transformed host cells are cells which have been transformed or transfected with the D5 receptor vectors constructed using recombinant DNA techniques. Transformed host cells ordinarily express the D5 receptor, but host cells transformed for purposes of cloning or amplifying the D5 receptor DNA need not express the D5 receptor. When expressed, the D5 receptor will typically be located in the host cell membrane.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leaders sequences, contiguous and in the same translational reading frame.

Cultures of cells derived from multicellular organisms are a desirable host for recombinant D5-dopamine receptor synthesis. In principal, any higher eukaryotic cell culture may be used, whether from vertebrate or invertebrate cell culture. However, mammalian cells are preferred, as illustrated in the Examples. Propagation of such cells in cell culture has become a routine procedure. See, Tissue Culture, Kruse & Patterson, eds. (Academic Press, 1973). Examples of useful host cell lines are COS-7 and 293 cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters of SV40 are useful because both are obtained easily from the virus as a fragment which also contains the SV40 viral origin of replication. See, Fiers et al., 1978, Nature 279: 113. Further, the human genomic D5 receptor promoter, control and/or signal sequences, may also be used, provided such control sequences are compatible with the host cell chosen.

An origin of replication may be provided either by construction of the vector to include an exogenous origin, such as may be derived from SV40 or other viral source (e.g., Polyoma, Adenovirus, VSV, or MPV), or may be provided by the host cell chromosomal replication mechanism. If the vector is integrated into the host cell chromosome, the latter may be sufficient.

D5-dopamine receptors made from cloned genes in accordance with the present invention may be used for screening compounds for D5 dopamine receptor activity, or for determining the amount of a dopaminergic drug in a solution (e.g., blood plasma or serum). For example, host cells may be transformed with a vector of the present invention, D5-dopamine receptors expressed thereby in that host, the cells lysed, and the membranes from those cells used to screen compounds for D5-dopamine receptor binding activity, as described in further detail in the following Examples. Competitive binding assays in which such procedures may be carried out are well known, as illustrated by the Examples below. By selection of host cells which do not ordinarily express a dopamine receptor, pure preparations of membranes containing D5 receptors can be obtained. Further, D5-dopamine receptor agonist and antagonists can be identified by transforming host cells with vectors of the present invention. Membranes obtained from such cells can be used in binding studies wherein the drug binding activity is monitored. Such cells must contain D5 protein in the plasma and other cell membranes. Procedures for carrying out assays such as these are also described in greater detail in the Examples which follow.

Cloned genes and vectors of the present invention are useful in molecular biology to transform cells which do not ordinarily express the D5-dopamine receptor to thereafter express this receptor. Such cells are useful as intermediates for making cell membrane preparations useful for receptor binding assays, which are in turn useful for drug screening. Further, genes and vectors of the present invention are useful in gene therapy, for replacing defective dopamine receptor genes in vivo. For such purposes, retroviral vectors as described in U.S. Pat. No. 4,650,764 to Temin and Watanabe or U.S. Pat. No. 4,861,719 to Miller may be employed. Cloned genes of the present invention, or fragments thereof, may also be used in gene therapy carried out homologous recombination or site-directed mutagenesis. See generally Smithies et al., 1985, Nature 917: 230–234; Thomas and Capecchi, 1987, Cell 51: 503–512; Bertling, 1987, Bioscience Reports 7:107–112.

Cloned genes of the present invention, and oligonucleotides derived therefrom, are useful for screening for restriction fragment length polymorphism (RFLP) associated with dopamine receptor-related genetic disorders.

Oligonucleotides of the present invention are useful as diagnostic tools for probing D5-receptor gene expression in tissue samples, including nervous tissue. For example, such tissue can be probed in situ with oligonucleotide probes carrying detectable groups by conventional autoradiography techniques to investigate native gene expression of this receptor or pathological conditions relating thereto. Such oligonucleotides can also be useful as diagnostic reagents. Further, chromosomes can be probed to investigate the presence or absence of a 5-dopamine receptor gene, and potential pathological conditions related thereto.

The Examples which follow are illustrative of specific embodiments of the invention, and various uses thereof. They are set forth for explanatory purposes only, and are not to be taken as limiting the invention.

EXAMPLE 1

Detection of a Novel Dopamine Receptor Homologous to the D1 Receptor in Human DNA A novel dopamine receptor gene homologous to the D1 receptor was detected in human genomic DNA. High molecular weight human genomic DNA was prepared using standard methods as described in Sambrook et al, 1989, *Molecular Cloning: A Laboratory Manual* (Cold Spring Harbor Laboratory:Cold Spring Harbor, N.Y.). 3 µg of such DNA were digested with the restriction enzyme EcoRI (Boehringer Mannheim, Indianapolis, Ind.). Digested DNA was precipitated and electrophoresed through a 0.7% vertical agarose gel, stained with ethidium bromide, photographed and processed for Southern blotting to a nitrocellulose filter (Schleicher and Schuell, Keene, N.H.). The filter was prehybridized at 37° C. for 16 hours in 50% formamide as described in Grandy et al., 1990, Amer. J. Hum. Genet. 47: 828–834, and hybridized with a $^{32}$P-labeled human D1 dopamine receptor gene probe. This probe was labeled with $^{32}$P by nick-translation (Bethesda Research Laboratories, Gaithersburg, Md.). The filter was hybridized with the human probe for 24 hrs, then washed at low stringency in 2×SSC (1× standard citrate saline=0.15M NaCl/0.015M Na-citrate, pH 7.0) and 0.1% SDS at 55° C. and exposed to X-ray film (Kodak, Rochester, N.Y.) for 48 hours with an intensifying screen at −70° C. After development of the autoradiographic film, the filter was washed at high stringency in 0.1×SSC and 0.1% SDS at 80° C. for 45 min and again exposed to X-ray film for 24 hours with an intensifying screen.

The results of this experiment are shown in FIG. 1. Under low-stringency conditions of washing, D1 probe hybridization detects a 5 kb cross-hybridizing band in genomic DNA that disappears at higher stringencies of washing. These results indicated the existence of an additional human D1-homologous gene, at least a portion of which resides on a 5 kb EcoRI genomic DNA fragment.

EXAMPLE 2

Screening a Human Genomic Library For a Novel Human D1-Homologous Dopamine Receptor Gene In order to isolate and characterize the novel human dopamine receptor gene homologous to the D1 receptor detected in human genomic DNA as described in Example 1, a partial human genomic library was constructed and screened. High molecular weight human genomic DNA was prepared from leukocytes as described in Sambrook et al., ibid., and 5 µg of this DNA were digested with EcoRI, precipitated and subjected to vertical electrophoresis in a 0.7% agarose gel. The gel was stained with ethidium bromide and the region corresponding to 5–6 kb [relative to the 1 kb ladder (Bethesda Research Laboratories)] was excised from the gel. DNA was extracted from agarose using Prep-a-Gene (Biorad, Richmond, Calif.), precipitated, ligated to EcoRI-digested lambda gt10 arms (Stratagene, LaJolla, Calif.) and packaged in vitro using GigaPak packaging extracts (Stratagene). Approximately 100,000 plaque-forming units from this library were placed on *E. coli* hfl-/C600 cells and duplicate filters (NEN Research Products, Boston, Mass.) of the resulting phage plaques were lifted. The filters were hybridized with a $^{32}$P-labeled nick-translated 3-kb genomic EcoRI/SacI fragment which contains the coding region of the human D1 dopamine receptor (Zhou et al., 1990, Nature 347: 76–809) as a probe for D1-homologous sequences. The hybridized filters were then washed and exposed to X-ray film as described in Example 1.

Following autoradiography of the hybridized phage plaques, 36 strong signals were observed in duplicate and ten of the corresponding phage were plaque purified. When their DNA was digested with EcoRI each one was found to contain a 5kb insert. This screening of the 5kb-enriched human genomic library yielded several positive phage which upon restriction analysis looked very similar. One of these clones, HGRI-6 was further characterized by sequencing. Nucleic acid sequences were determined in both orientations by the Sanger dideoxy method using Sequenase (US Biochemicals, Cleveland, Ohio) primed with synthetic oligonucleotides using standard methods. Sequence analysis was aided by Intelligenetics (Mountain View, Calif.) software run on a MicroVAX computer.

These results are presented in FIGS. 2A through 2L. This Figure illustrates the nucleic acid sequence of clone HGRI-6 (SEQ ID No:3) in comparison with the sequence of the human D1 dopamine receptor and two additional clones to be discussed herein. The HGRI-6 clone was found to be 1444 bps in length and 65% identical to the human D1 receptor gene. However, this gene contained a stop codon in-frame corresponding to residue 152. The presence of this in-frame stop codon, as well as the lack of typical splice site consensus sequences expected to be found in a functional gene, suggested that this clone was a pseudogene. We termed this pseudogene D5ψ1.

EXAMPLE 3

Identification of D1-Homologous Dopamine Receptor Genes Following In Vitro Amplification In order to establish whether the human genome contains a functional homologue to HGRI-6, in vitro amplification of human genomic DNA insert sequences were performed on DNA prepared from the remaining nine original genomic phage clones using the polymerase chain reaction (Salki et al., 1988, Science 239: 487–491). The two synthetic primers used for polymerase chain reaction (PCR) were based on HGRI-6 sequences located in the receptor's highly conserved TMDs III and V. PCR was performed in an automated temperature cycling devise (Tempcycler, Coy, Ann Arbor, Mich.) using 1 unit of Replinase (NEN Research Products, Boston, Mass.) on 1 ng of phage template DNA with 50 pmol of each synthetic primer. The primer sequences were:

5'- CCGAATTCGCCTTCGACATCATGTGC-3' in TMD III [SEQ.ID-No: 5]; and

5'- CCGGATCCGTCACGATCATGATGGC-3' in TMD V [SEQ.ID No: 6].

Amplification was achieved after 25 cycles of denaturation at 95° C. for 1 min; annealing for 2 min at 55° C. and extension for 3 min at 72° C. The products of the PCR were gel purified, digested with both EcoRI and BamHI, ligated into appropriately restriction enzyme digested cloning/sequencing vectors M13mp18 and 19 and sequenced with Sequenase (US Biochemicals) as described in Example 2.

Nucleotide sequence analysis of the PCR products revealed two additional D1-homologous genomic clones, HGRI-4 and HGRI-8. The complete nucleotide sequences of these clones were determined as described in Example 2 and are shown in FIGS. 2A through 2L. The nucleic acid sequence of clone HGRI-8 (SEQ ID No:4) is 98% identical with clone HGRI-6. However, clone HGRI-8 was also found to contain an in-frame TGA stop codon in place of residue 152, and so most probably represents a second pseudogene (termed D5ψ2). The other clone, HGRI4 (SEQ ID No: 1), is 95% identical to HGRI-6. Clone HGRI-4 has an uninterrupted open reading frame of 1434 bps. Of the three genes identified, only HGRI4 has an open reading frame of extent sufficient to encode a G protein-coupled receptor (FIG. 2). These results indicate that we have isolated a novel human dopamine receptor gene and 2 related pseudogenes. This conclusion was confirmed by nucleic acid sequencing and comparison of the sequence of clone HGRI4 with the sequences of other dopamine and catecholamine receptor genes (see Example 4).

EXAMPLE 4

DNA Sequence Analysis of the Human D5 Dopamine Receptor Gene

Our conclusion that we had isolated a novel human dopamine receptor gene and two pseudogenes was confirmed by nucleic acid sequencing and comparison of these sequences to those of other dopamine and catecholamine receptor genes. Sequencing was performed as described in Example 2 above. The results of these experiments are shown in FIGS. 3A and 3B.

The deduced amino acid sequence of clone HGRI-4 (SEQ ID No:2) consists of 1434 residues (relative molecular mass, $M_r$=52950) which are organized into seven putative transmembrane domains (TMDs) that are from 56% (TMD I) to 96% (TMD V) identical to the corresponding TMDs found in the human D1 receptor gene. Overall the receptor's amino acid sequence is 49% identical to the human D1 receptor. Six asparagine (Asn) residues represent potential N-linked glycosylation sites and the presence of one of them near the N-terminus of the protein ($Asn^6$) is a structural feature shared by all of the cloned dopamine receptors. Another potential N-glycosylation site, $Asn^{351}$, is located in TMD VII and is also seen in both human and rat D1 receptors. Of the remaining four sites, $Asn^{74}$ and $Asn^{388}$ are located in the putative extracellular loop between TMDs IV and V. The deduced HGRI-4 receptor sequence also contains two cysteine residues ($Cys^{113}$ and $Cys^{217}$) which are conserved among dopamine receptors. These are located in the second and third putative extracellular loops and may be involved in the formation of a disulfide bond which could be important for stabilizing the receptor's tertiary structure.

The deduced receptor sequence also contains several potential protein kinase phosphorylation target sites: four for protein kinase A (Kemp & Pearson, 1990, TIBS 15: 342–346) and three for protein kinase C (Graff et al., 1989, J. Biol. Chem. 264: 11912–11919). Interestingly, five of these consensus sequences are located in the putative third cytoplasmic loop of the molecule. This domain is thought to be important for the coupling of the receptor to G proteins (O'Dowd et al., 1988, J. Biol. Chem. 263: 15985–15992) suggesting that these sites may play an important regulatory role. In addition there are several serine and threonine residues in the carboxyl-terminal potion of the HGRI-4 receptor protein which may be phosphorylated by receptor kinase (Bouvier et al., 1988, Nature 333: 370–373). The presence of $Cys^{375}$ at the molecule's carboxyl terminus may also permit palmitoylation of this domain of the receptor, providing a point of attachment to the plasma membrane (see, Ovchinnikov et al., 1988, FEBS Lett. 230: 1–5; O'Dowd et al., 1989, J. Biol. Chem. 264: 7564–7569).

Our comparison of the deduced aminoacid sequence of clone HGRI-4 with the four other known human dopamine receptors is presented in FIGS. 3A and 3B. This comparison reveals considerable conservation in the putative TMDs of all dopamine receptor proteins, as expected for receptors which bind the same ligand. Overall the seven TMDs of HGRI-4 share 82% identity with the human D 1 dopamine receptor. Noteworthy among the conserved residues are $Asp^{120}$, $Ser^{229}$ and $Ser^{233}$, amino acids found in TMDs III and V of all cloned catecholamine receptors. These residues are thought to coordinate the amino and catechol hydroxyl moieties of catecholamine ligands (see, Dixon et al., 1987, Nature 326: 73–77; Strader et al., 1989, J. Biol. Chem. 264: 13572–13578). In addition, the lengths of the putative third cytoplasmic loop and carboxyl tail of clone HGRI-4 are similar to their counterparts in the human D1 dopamine receptor. Together with the highly conserved TMDs, these structural characteristics strongly suggested that this molecule is a new D1-like dopamine receptor which couples to G proteins.

EXAMPLE 5

Expression of the Human D5 Dopamine Receptor and Its Pseudogenes

The coding sequences of the human D5 dopamine receptor and each of its pseudogenes were amplified in vitro from their corresponding phage clones and used to synthesize expression cassettes using PCR. PCR was performed on phage HGRI-4, HGRI-6 and HGRI-8 DNA as described above with the following 5' and 3' oligonucleotide primers:

SENSE: 5'-CCGTCGACGATCGCGCACAAACCGAC-3' (SEQ ID No: 7)

ANTISENSE: 5'-CCGTCGACAGTACTGGAAAGGCATGTAT-3' (SEQ ID No: 8)

PCR was performed as described in Example 3. The products of the PCR were gel purified, digested with SalI and ligated into the vector pGEMBlue (Promega Biotech, Madison, Wis.). The ligation products were used to transform E. coli strain XL-1 cells (Stratagene) and clones with inserts in the proper orientation were identified, isolated and digested with HindIII and BamHI. The 1.56 kb inserts representing each gene were isolated and ligated into the transient expression vector pBC12 BI (as described in Cullen, 1987, Methods Enzymol. 152: 684–704, (Berger and Kimmel, eds.) Academic Press: New York, N.Y.).

One of the resulting constructs, pBCHGRI-4, was used to establish the pharmacological profile of binding of agonists and antagonists of the putative receptor encoded by HGRI-4, transiently expressed after transfection of this construct into COS-7 cells. Whether or not pBCHGRI-4 encodes a functional receptor was examined by its ability to stimulate intracellular cyclic adenosine monophosphate (cAMP) accumulation in the human embryonic kidney cell line 293. The putative pseudogenes, HGRI-6 and HGRI-8, as well as the human D1 dopamine receptor gene, were also transiently expressed in these cells. A modified calcium phosphate method was used for the transfection of monkey COS-7 and human 293 cells as described by Chen and Okayama (1987, Molec. Cell. Biol. 7: 2745–2752). These transfectants were used to characterize the pharmacological properties of the D5 dopamine receptor and to confirm the non-functional nature of each of its two pseudogenes, as described in Example 6.

EXAMPLE 6

Expression and Pharmacological Evaluation of Dopamine and Dopamine-Antagonist Binding of the D5 Dopamine Receptor The transfectants generated by the methods of Example 5 were used to characterize the pharmacological properties of the D5 dopamine receptor and to confirm the non-functional nature of each of its two pseudogenes. COS-7 cell transfectants were used for the purification of membranes enriched for D5 dopamine receptor content. These cells were previously shown to lack the ability to bind the D1 receptor-specific antagonist 8CH23390 (Zhou et al., 1990, Nature 347: 76–80). 293 cell transfectants were used to evaluate the physiological effects of D5 receptor binding with various ligands, particularly the effect on cellular cAMP levels that reflect activation of the cellular enzyme adenyl cyclase. Messenger RNA (mRNA) expression of the D5-containing construct, each of the putative pseudogene-containing constructs and the D1 receptor gene construct was confirmed by Northern hybridization of transfectant mRNA as described in Sambrook et al., ibid.

COS-7 and 293 cells were transfected with an expression vector containing the human D5 dopamine receptor gene corresponding to clone HGRI-4 under the control of the Rous sarcoma virus-derived long terminal repeat promoter and in the proper orientation for expression (pBCHGRI-4). For membrane assays, COS-7 cells were washed twice with HOB buffer (15 mM Tris HCl, pH 7.4, 2.5 mM $MgCl_2$, 1 mM EDTA) 48 hours post-transection, harvested, homogenized in a ConTorque Homogenizer (Eberbach, Ann Arbor, Mich.) at 4° C. in TEM buffer (25 mM Tris HCl, pH 7.4, 67 mm $MgCl_2$, 1 mM EDTA) and centrifuged at 800 g for 10 min. The supernatant was saved and the pellet was resuspended in TEM buffer and centrifugation repeated. The supernatants were pooled and centrifuged at 100,000 g for 1 hour. The resulting pellet was resuspended in TEM buffer and the protein concentration was determined by a modification of the method of Lowry (Markwell et al., 1978, Anal. Biochem. 87: 206–210) and stored in small aliquots at –70° C. until use.

Pharmacological evaluations, including analysis of agonist and antagonist binding assays were performed in duplicate and competition curves in triplicate, with between 8–12 and 12–18 different drug concentrations for antagonists and agonists, respectively. Samples were analyzed in reaction volumes of 500 µl of a buffer containing 50 mm TrisHCl, pH 7.4, 0.9% NaCl, 0.025% ascorbic acid, 0.001% bovine serum albumin and various concentrations of the dopamine agonist ($^3$H)SCH23390 (specific activity, 69 Ci/mmol; Amersham, Arlington Heights, Ill.) for saturation binding experiments. For competition experiments the binding of 0.7–1.0 nM ($^3$H)SCH23390 was inhibited by various concentrations of unlabeled drugs. The binding reactions were initiated by the addition of 5–50 µg of transfectant membranes and were performed at 37° C. for 1 hour. Nonspecific binding was defined in the presence of 5 µM (+)-butaclamol. Samples were filtered through glass fiber filters (Schleicher and Schuell No. 32) and washed three times with 4 ml of ice cold 50 mm TrisHCl buffer at pH 7.4. Radioactivity was counted using a Packard 2200 CA TriCarb liquid scintillation analyzer. The 50% inhibitory concentration values ($IC_{50}$) calculated from the curves were convened to $K_i$ values as described in Zhou et al., 1990, Nature 347: 76–80. A GRAPHPAD computer program was used for data analysis and curve fitting (as described in Zhou et al, ibid.) For cAMP assays, 293 cells were transfected, stimulated with various drugs and intracellular cAMP accumulation quantitated as described in Zhou et al., ibid.

Figure 4:
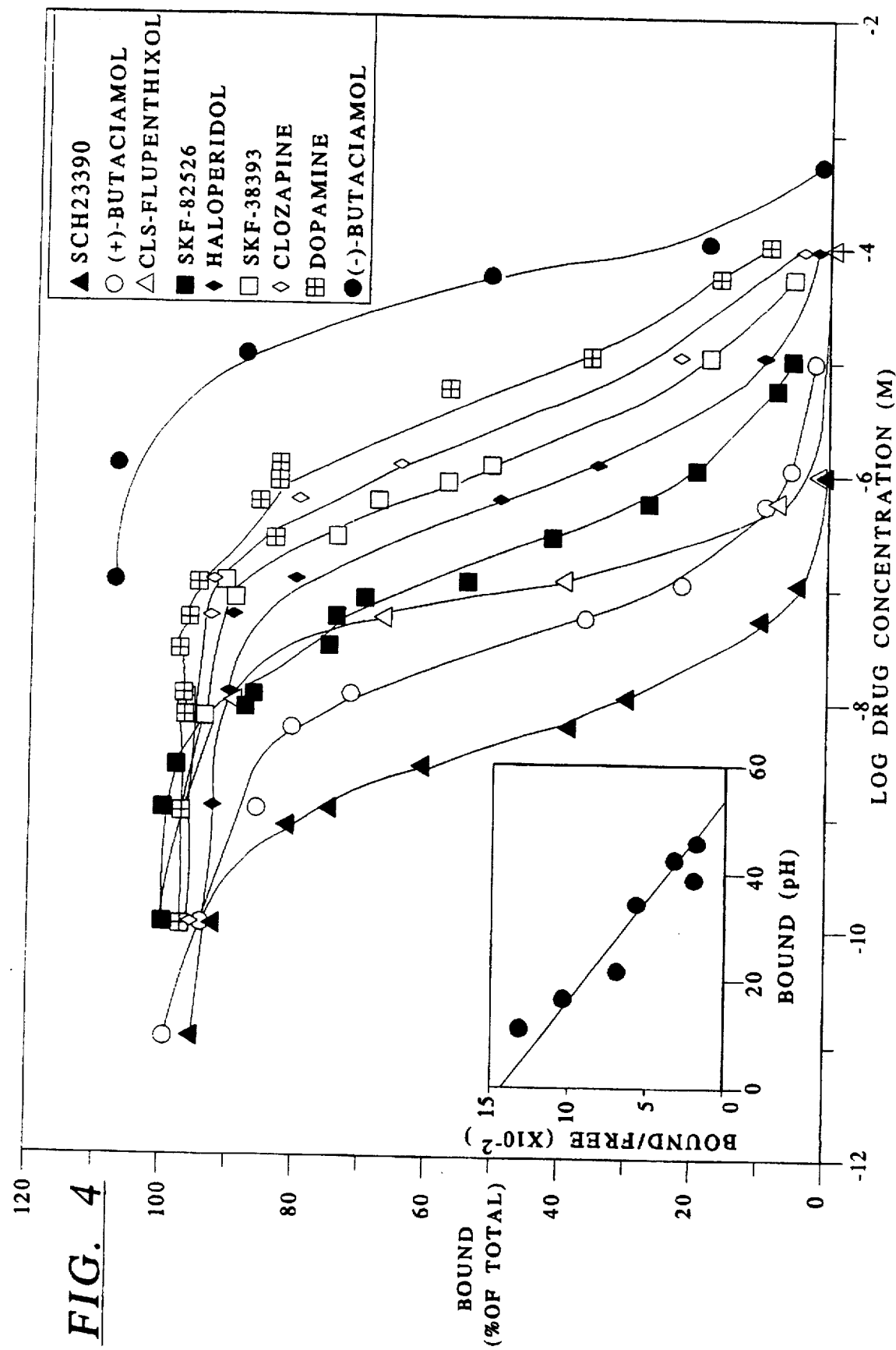
FIG. 4. Binding of [$^3$H]SCHB23390 to membranes prepared from COS-7 cells transiently expressing pBCHGRI-4. (Inset) Scratchard transformation of the saturation binding data.
Figure 5:
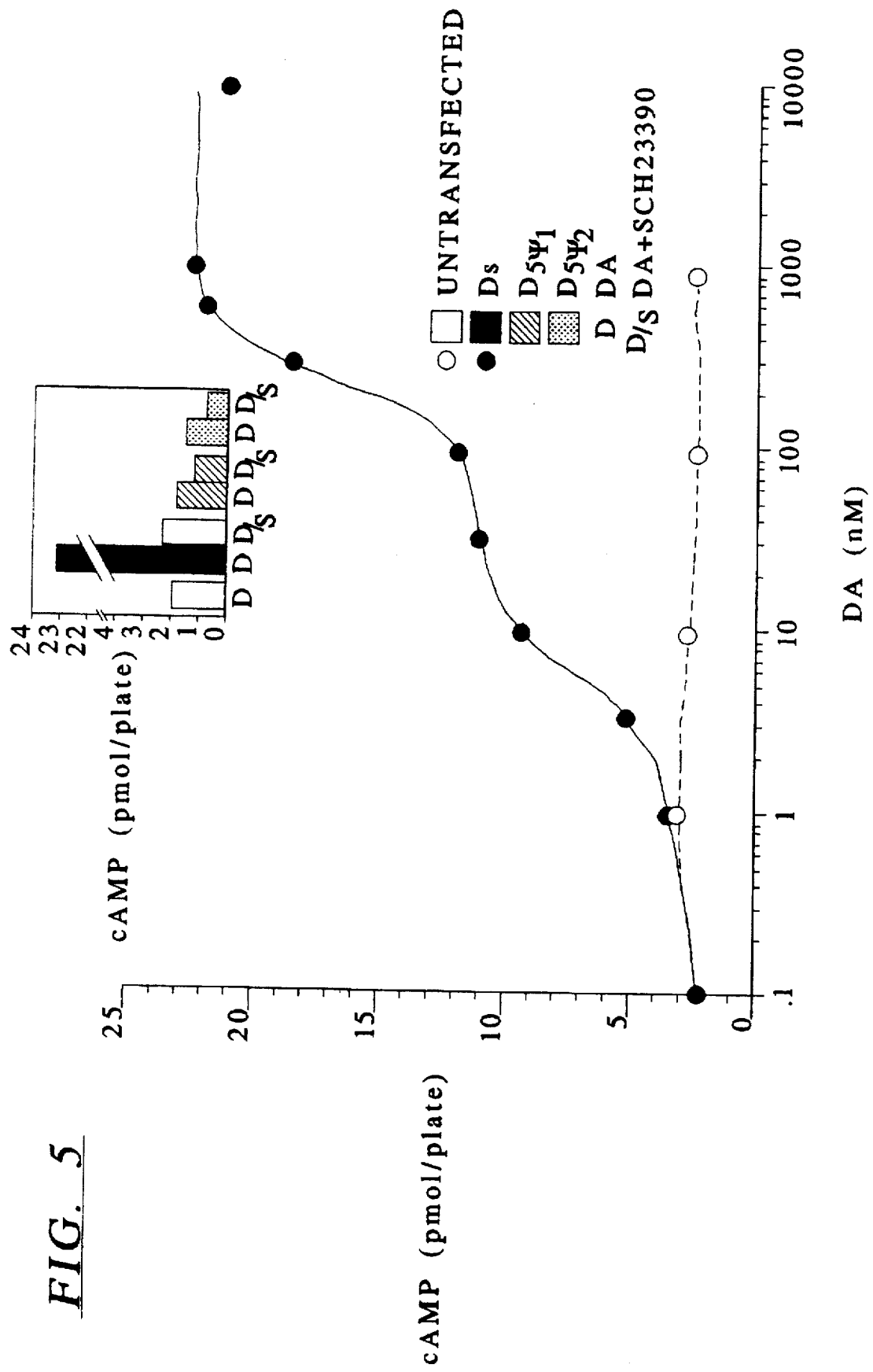
FIG. 5. Dopamine-stimulated cAMP accumulation in human 293 cells expressing the D5 receptor. (Inset) 250 nM SCH23390 was used to antagonize both dopamine-stimulated and SKF38393-stimulated cAMP production in 293 cells expressing each of the three D5 dopamine receptor genes.
Figure 6:
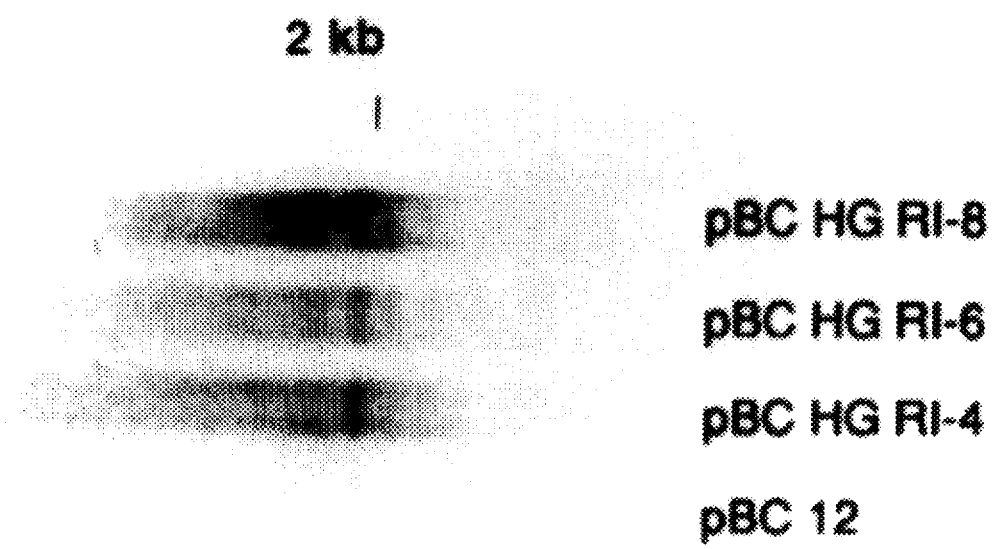
FIG. 6. Northern blot of COS-7 cell transfectants demonstrating transient expression of the human D5 dopamine receptor gene and 2 related pseudogenes. Total RNA was prepared from cells that had been transfected with one of the following constructions: pBC12 BI, pBCHGRI-4, pBCHGRI-6, or pBCHGRI-8. Each lane contains 5 µg of total RNA. Hybridization was performed with a 32P-labeled fragment spanning TMD III-V of HGRI-4 as a probe. The numbers on the left were extrapolated from the relative mobility of RNA size markers.

The results of these experiments are presented in FIG. 5 and Table 1, and a representative Northern hybridization experiment is illustrated in FIG. 6. The extensive sequence conservation observed between the D1 and D5 TMDs is reflected in their pharmacological profiles. Membranes were prepared from each of the transfected cell populations and analyzed for their ability to bind ($^3$H)SCH23390. Membranes prepared from cells transfected with pBCHGRI-4 expressed high levels of saturable ($^3$H)SCH23390 binding upon Scatchard analysis with an average dissociation constant ($K_d$) of 0.35 nM (n+7) and an average $B_{max}$ of 4 pmol/mg protein (n =7) (FIG. 4A, insert). These values are similar to those obtained in parallel experiments with the human D1 dopamine receptor. In contrast, membranes prepared from cells transfected with each of the two putative pseudogenes failed to bind ($^3$H)SCH23390 even though their mRNA was expressed at levels equivalent to the levels of pBCHGRI4 (FIG. 6).

In order to characterize the ligand-binding profile of the receptor encoded by HGRI-4, ($^3$H)SCH23390 was used in competition experiments with both antagonists and agonists (FIG. 4A and Table 1). The antagonist data was fit best assuming one class of binding site. Based on these studies the rank order of antagonist potency was:

SCH23390 (0.6 nM)>(+)-butaclamol (9.1 mM)>cis-flupenthixol (23.6 nM)> haloperidol (156 mM)>clozapine (406 mM)>>(−)-butaclamol (>10 μM)

This is the same relative rank order of potency as previously observed for the human D1 and the HGRI4 encoded receptors. The human D1 dopamine receptor has approximately a 5-fold higher affinity for (+)-butaclamol than does the pBCHGRI4 encoded receptor. When the three agonists were evaluated in competition experiments (FIG. 4A) all three curves had slopes that were less than unity (0.6). Based on these results the date were fit assuming the presence of both high and low affinity sites.

The rank order of potency for the agonists was:

SKF82526 (fenoldopam)>SDKF38393>dopamine with average (n=3) $K_i$'s of 0.6 nM and 27 nM, 0.52 nM and 469 nM, and 12.8 nM and 1806 nM, respectively. In parallel experiments the human D1 receptor also displayed high and low affinity binding sites for dopamine but the avenge (n=2) $K_i$ values (32 nM for the high affinity site and 9109 nM for the low affinity site) are higher than observed for the D5 dopamine receptor. Taken together the pharmacological data strongly suggest that pBCHGRI4 encodes a D 1-like binding site with a higher affinity for dopamine that D1.

Whether or not pBCHGRI-4 encodes a functional receptor was examined by its ability to stimulate intracellular cAMP accumulation in the human embryonic kidney cell line 293. Previously we had demonstrated that these cells do not express endogenous dopamine receptors (Zhou et at., ibid.). The cells that received pBCHGRI4 displayed a concentration-dependent and saturable increase in intracellular cAMP levels when exposed to dopamine (FIG. 4B). Furthermore, this stimulation could be antagonized by 250nM SCI-I23390 (FIG. 4B, inset). Of particular interest is the shape of the dome/cAMP dose-response curve. The data from three independent experiments were best fit by a two site model and two half maximal stimulation concentrations ($EC_{50}$) for dopamine were calculated; these were 5.0 nM and 275 nM, respectively. In parallel experiments the two putative pseudogenes pBCHGRI-6 and pBCHGRI-8 were also transfected into 293 cells. The 293 cells transfected with either pBCHGRI-6 or pBCHGRI-8 showed no significant accumulation of intracellular cAMP when exposed to agonist (FIG. 4B, insert). These results further support the conclusion that these clones represent D5 processed pseudogenes.

The results of these experiments indicate that we have successfully isolated a novel human D5 dopamine receptor gene having unique pharmacological properties. Our results also indicate that this gene is accompanied in the human genome by two related by distinct processed pseudogenes. The extensive sequence conservation between the D1 and D5 TMDs is reflected in their pharmacological profiles. Both bind ($^3$H)SCH23390 with high affinity ($K_d$=0.35 nM) and basically share the same rank order of ligand potency with two notable differences: the human D5 receptor shows a 5-fold lower affinity for the antagonist (+) butaclamol and a 10-fold higher affinity for dopamine. Furthermore, the two receptors are distinguishable at the second messenger level: the D5 receptor is able to stimulate adenylyl cyclase at dopamine concentrations which are 30-fold lower than required by the D 1 receptor in the same 293 cell line. The results confirm our isolation of a novel human dopamine receptor gene and 2 related pseudogenes.

What we claim is:

1. A homogeneous composition of a 53 kilodalton human D5 dopamine receptor having an amino acid sequence comprising the sequence shown as SEQ ID No.:2.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 1673 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: CDS
( B ) LOCATION: 148..1578

( x i ) SEQUENCE DESCRIPTION: SEQ ID NO:1:

-continued

| | | | | | | | | | | | |
|---|---|---|---|---|---|---|---|---|---|---|---|
| CCCGGCGCAG | CTCATGGTGA | GCGCCTCTGG | GGCTCGAGGG | TCCCTTGGCT | GAGGGGGCGC | | | | | | 60 |
| ATCCTCGGGG | TGCCCGATGG | GGCTGCCTGG | GGGTCGCAGG | GCTGAAGTTG | GGATCGCGCA | | | | | | 120 |
| CAAACCGACC | CTGCAGTCCA | GCCCGAA | ATG | CTG | CCG | CCA | GGC | AGC | AAC | GGC | 171 |
| | | | Met | Leu | Pro | Pro | Gly | Ser | Asn | Gly | |
| | | | 1 | | | | 5 | | | | |

| ACC | GCG | TAC | CCG | GGG | CAG | TTC | GCT | CTA | TAC | CAG | CAG | CTG | GCG | CAG | GGG | 219 |
|---|---|---|---|---|---|---|---|---|---|---|---|---|---|---|---|---|
| Thr | Ala | Tyr | Pro | Gly | Gln | Phe | Ala | Leu | Tyr | Gln | Gln | Leu | Ala | Gln | Gly | |
| | 10 | | | | 15 | | | | | | 20 | | | | | |

| AAC | GCC | GTG | GGG | GGC | TCG | GCG | GGG | GCA | CCG | CCA | CTG | GGG | CCC | TCA | CAG | 267 |
|---|---|---|---|---|---|---|---|---|---|---|---|---|---|---|---|---|
| Asn | Ala | Val | Gly | Gly | Ser | Ala | Gly | Ala | Pro | Pro | Leu | Gly | Pro | Ser | Gln | |
| 25 | | | | 30 | | | | | 35 | | | | | | 40 | |

| GTG | GTC | ACC | GCC | TGC | CTG | CTG | ACC | CTA | CTC | ATC | ATC | TGG | ACC | CTG | CTG | 315 |
|---|---|---|---|---|---|---|---|---|---|---|---|---|---|---|---|---|
| Val | Val | Thr | Ala | Cys | Leu | Leu | Thr | Leu | Leu | Ile | Ile | Trp | Thr | Leu | Leu | |
| | | | | 45 | | | | | 50 | | | | | | 55 | |

| GGC | AAC | GTG | CTG | GTG | TGC | GCA | GCC | ATC | GTG | CGG | AGC | CGC | CAC | CTG | CGC | 363 |
|---|---|---|---|---|---|---|---|---|---|---|---|---|---|---|---|---|
| Gly | Asn | Val | Leu | Val | Cys | Ala | Ala | Ile | Val | Arg | Ser | Arg | His | Leu | Arg | |
| | | | 60 | | | | | 65 | | | | | 70 | | | |

| GCC | AAC | ATG | ACC | AAC | GTC | TTC | ATC | GTG | TCT | CTG | GCC | GTG | TCT | GAC | CTT | 411 |
|---|---|---|---|---|---|---|---|---|---|---|---|---|---|---|---|---|
| Ala | Asn | Met | Thr | Asn | Val | Phe | Ile | Val | Ser | Leu | Ala | Val | Ser | Asp | Leu | |
| | | 75 | | | | | 80 | | | | | 85 | | | | |

| TTC | GTG | GCG | CTG | CTG | GTC | ATG | CCC | TGG | AAG | GCA | GTC | GCC | GAG | GTG | GCC | 459 |
|---|---|---|---|---|---|---|---|---|---|---|---|---|---|---|---|---|
| Phe | Val | Ala | Leu | Leu | Val | Met | Pro | Trp | Lys | Ala | Val | Ala | Glu | Val | Ala | |
| | 90 | | | | | 95 | | | | | 100 | | | | | |

| GGT | TAC | TGG | CCC | TTT | GGA | GCG | TTC | TGC | GAC | GTC | TGG | GTG | GCC | TTC | GAC | 507 |
|---|---|---|---|---|---|---|---|---|---|---|---|---|---|---|---|---|
| Gly | Tyr | Trp | Pro | Phe | Gly | Ala | Phe | Cys | Asp | Val | Trp | Val | Ala | Phe | Asp | |
| 105 | | | | 110 | | | | | 115 | | | | | 120 | | |

| ATC | ATG | TGC | TCC | ACT | GCC | TCC | ATC | CTG | AAC | CTG | TGC | GTC | ATC | AGC | GTG | 555 |
|---|---|---|---|---|---|---|---|---|---|---|---|---|---|---|---|---|
| Ile | Met | Cys | Ser | Thr | Ala | Ser | Ile | Leu | Asn | Leu | Cys | Val | Ile | Ser | Val | |
| | | | | 125 | | | | | 130 | | | | | 135 | | |

| GAC | CGC | TAC | TGG | GCC | ATC | TCC | AGG | CCC | TTC | CGC | TAC | AAG | CGC | AAG | ATG | 603 |
|---|---|---|---|---|---|---|---|---|---|---|---|---|---|---|---|---|
| Asp | Arg | Tyr | Trp | Ala | Ile | Ser | Arg | Pro | Phe | Arg | Tyr | Lys | Arg | Lys | Met | |
| | | | 140 | | | | | 145 | | | | | 150 | | | |

| ACT | CAG | CGC | ATG | GCC | TTG | GTC | ATG | GTC | GGC | CTG | GCA | TGG | ACC | TTG | TCC | 651 |
|---|---|---|---|---|---|---|---|---|---|---|---|---|---|---|---|---|
| Thr | Gln | Arg | Met | Ala | Leu | Val | Met | Val | Gly | Leu | Ala | Trp | Thr | Leu | Ser | |
| | | 155 | | | | | 160 | | | | | 165 | | | | |

| ATC | CTC | ATC | TCC | TTC | ATT | CCG | GTC | CAG | CTC | AAC | TGG | CAC | AGG | GAC | CAG | 699 |
|---|---|---|---|---|---|---|---|---|---|---|---|---|---|---|---|---|
| Ile | Leu | Ile | Ser | Phe | Ile | Pro | Val | Gln | Leu | Asn | Trp | His | Arg | Asp | Gln | |
| | 170 | | | | | 175 | | | | | 180 | | | | | |

| GCG | GCC | TCT | TGG | GGC | GGG | CTG | GAC | CTG | CCA | AAC | AAC | CTG | GCC | AAC | TGG | 747 |
|---|---|---|---|---|---|---|---|---|---|---|---|---|---|---|---|---|
| Ala | Ala | Ser | Trp | Gly | Gly | Leu | Asp | Leu | Pro | Asn | Asn | Leu | Ala | Asn | Trp | |
| 185 | | | | 190 | | | | | 195 | | | | | 200 | | |

| ACG | CCC | TGG | GAG | GAG | GAC | TTT | TGG | GAG | CCC | GAC | GTG | AAT | GCA | GAG | AAC | 795 |
|---|---|---|---|---|---|---|---|---|---|---|---|---|---|---|---|---|
| Thr | Pro | Trp | Glu | Glu | Asp | Phe | Trp | Glu | Pro | Asp | Val | Asn | Ala | Glu | Asn | |
| | | | | 205 | | | | | 210 | | | | | 215 | | |

| TGT | GAC | TCC | AGC | CTG | AAT | CGA | ACC | TAC | GCC | ATC | TCT | TCC | TCG | CTC | ATC | 843 |
|---|---|---|---|---|---|---|---|---|---|---|---|---|---|---|---|---|
| Cys | Asp | Ser | Ser | Leu | Asn | Arg | Thr | Tyr | Ala | Ile | Ser | Ser | Ser | Leu | Ile | |
| | | | 220 | | | | | 225 | | | | | 230 | | | |

| AGC | TTC | TAC | ATC | CCC | GTT | GCC | ATC | ATG | ATC | GTG | ACC | TAC | ACG | CGC | ATC | 891 |
|---|---|---|---|---|---|---|---|---|---|---|---|---|---|---|---|---|
| Ser | Phe | Tyr | Ile | Pro | Val | Ala | Ile | Met | Ile | Val | Thr | Tyr | Thr | Arg | Ile | |
| | | 235 | | | | | 240 | | | | | 245 | | | | |

| TAC | CGC | ATC | GCC | CAG | GTG | CAG | ATC | CGC | AGG | ATT | TCC | TCC | CTG | GAG | AGG | 939 |
|---|---|---|---|---|---|---|---|---|---|---|---|---|---|---|---|---|
| Tyr | Arg | Ile | Ala | Gln | Val | Gln | Ile | Arg | Arg | Ile | Ser | Ser | Leu | Glu | Arg | |
| | 250 | | | | | 255 | | | | | 260 | | | | | |

| GCC | GCA | GAG | CAC | GCG | CAG | AGC | TGC | CGG | AGC | AGC | GCA | GCC | TGC | GCG | CCC | 987 |
|---|---|---|---|---|---|---|---|---|---|---|---|---|---|---|---|---|
| Ala | Ala | Glu | His | Ala | Gln | Ser | Cys | Arg | Ser | Ser | Ala | Ala | Cys | Ala | Pro | |
| 265 | | | | 270 | | | | | 275 | | | | | 280 | | |

| GAC | ACC | AGC | CTG | CGC | GCT | TCC | ATC | AAG | AAG | GAG | ACC | AAG | GTT | CTC | AAG | 1035 |
|---|---|---|---|---|---|---|---|---|---|---|---|---|---|---|---|---|
| Asp | Thr | Ser | Leu | Arg | Ala | Ser | Ile | Lys | Lys | Glu | Thr | Lys | Val | Leu | Lys | |
| | | | | 285 | | | | | 290 | | | | | 295 | | |

| | | | | | | | | | | | | | | | | |
|---|---|---|---|---|---|---|---|---|---|---|---|---|---|---|---|---|
| ACC | CTG | TCG | GTG | ATC | ATG | GGG | GTC | TTC | GTG | TGT | TGC | TGG | CTG | CCC | TTC | 1083 |
| Thr | Leu | Ser | Val 300 | Ile | Met | Gly | Val | Phe 305 | Val | Cys | Cys | Trp | Leu 310 | Pro | Phe | |
| TTC | ATC | CTT | AAC | TGC | ATG | GTC | CCT | TTC | TGC | AGT | GGA | CAC | CCT | GAA | GGC | 1131 |
| Phe | Ile | Leu 315 | Asn | Cys | Met | Val | Pro 320 | Phe | Cys | Ser | Gly | His 325 | Pro | Glu | Gly | |
| CCT | CCG | GCC | GGC | TTC | CCC | TGC | GTC | AGT | GAG | ACC | ACC | TTC | GAC | GTC | TTC | 1179 |
| Pro | Pro 330 | Ala | Gly | Phe | Pro | Cys 335 | Val | Ser | Glu | Thr | Thr 340 | Phe | Asp | Val | Phe | |
| GTC | TGG | TTC | GGC | TGG | GCT | AAC | TCC | TCA | CTC | AAC | CCC | GTC | ATC | TAT | GCC | 1227 |
| Val 345 | Trp | Phe | Gly | Trp | Ala 350 | Asn | Ser | Ser | Leu | Asn 355 | Pro | Val | Ile | Tyr | Ala 360 | |
| TTC | AAC | GCC | GAC | TTT | CAG | AAG | GTG | TTT | GCC | CAG | CTG | CTG | GGG | TCG | AGC | 1275 |
| Phe | Asn | Ala | Asp | Phe 365 | Gln | Lys | Val | Phe | Ala 370 | Gln | Leu | Leu | Gly | Ser 375 | Ser | |
| CAC | TTC | TGC | TCC | CGC | ACG | CCG | GTG | GAG | ACG | GTG | AAC | ATC | AGC | AAT | GAG | 1323 |
| His | Phe | Cys | Ser 380 | Arg | Thr | Pro | Val | Glu 385 | Thr | Val | Asn | Ile | Ser 390 | Asn | Glu | |
| CTC | ATC | TCC | TAC | AAC | CAA | GAC | ATC | GTC | TTC | CAC | AAG | GAA | ATC | GCA | GCT | 1371 |
| Leu | Ile | Ser 395 | Tyr | Asn | Gln | Asp | Ile 400 | Val | Phe | His | Lys | Glu 405 | Ile | Ala | Ala | |
| GCC | TAC | ATC | CAC | ATG | ATG | CCC | AAC | GCC | GTT | ACC | CCC | GGC | AAC | CGG | GAG | 1419 |
| Ala | Tyr 410 | Ile | His | Met | Met 415 | Pro | Asn | Ala | Val | Thr 420 | Pro | Gly | Asn | Arg | Glu | |
| GTG | GAC | AAC | GAC | GAG | GAG | GAG | GGT | CCT | TTC | GAT | CGC | ATG | TTC | CAG | ATC | 1467 |
| Val 425 | Asp | Asn | Asp | Glu | Glu 430 | Glu | Gly | Pro | Phe | Asp 435 | Arg | Met | Phe | Gln | Ile 440 | |
| TAT | CAG | ACG | TCC | CCA | GAT | GGT | GAC | CCT | GTT | GCT | GAG | TCT | GTC | TGG | GAG | 1515 |
| Tyr | Gln | Thr | Ser | Pro 445 | Asp | Gly | Asp | Pro | Val 450 | Ala | Glu | Ser | Val | Trp 455 | Glu | |
| CTG | GAC | TGC | GAG | GGG | GAG | ATT | TCT | TTA | GAC | AAA | ATA | ACA | CCT | TTC | ACC | 1563 |
| Leu | Asp | Cys | Glu 460 | Gly | Glu | Ile | Ser | Leu 465 | Asp | Lys | Ile | Thr | Pro 470 | Phe | Thr | |
| CCG | AAT | GGA | TTC | CAT | TAAACTGCAT | TAAGAAACCC | CCTCATGGAT | CTGCATAACC | | | | | | | | 1618 |
| Pro | Asn | Gly | Phe | His 475 | | | | | | | | | | | | |

GCACAGACAC TGACAAGCAC GCACACACAC GCAAATACAT GCCTTTCCAG TACTG     1673

(2) INFORMATION FOR SEQ ID NO:2:

(i) SEQUENCE CHARACTERISTICS:
       (A) LENGTH: 477 amino acids
       (B) TYPE: amino acid
       (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met 1 | Leu | Pro | Pro | Gly 5 | Ser | Asn | Gly | Thr | Ala 10 | Tyr | Pro | Gly | Gln | Phe Ala 15 |
| Leu | Tyr | Gln | Gln 20 | Leu | Ala | Gln | Gly | Asn 25 | Ala | Val | Gly | Gly | Ser 30 | Ala Gly |
| Ala | Pro | Pro 35 | Leu | Gly | Pro | Ser | Gln 40 | Val | Val | Thr | Ala | Cys 45 | Leu | Leu Thr |
| Leu | Leu 50 | Ile | Ile | Trp | Thr | Leu 55 | Leu | Gly | Asn | Val | Leu 60 | Val | Cys | Ala Ala |
| Ile 65 | Val | Arg | Ser | Arg | His 70 | Leu | Arg | Ala | Asn | Met 75 | Thr | Asn | Val | Phe Ile 80 |
| Val | Ser | Leu | Ala | Val 85 | Ser | Asp | Leu | Phe | Val 90 | Ala | Leu | Leu | Val | Met Pro 95 |

```
Trp Lys Ala Val Ala Glu Val Ala Gly Tyr Trp Pro Phe Gly Ala Phe
        100             105             110
Cys Asp Val Trp Val Ala Phe Asp Ile Met Cys Ser Thr Ala Ser Ile
        115             120             125
Leu Asn Leu Cys Val Ile Ser Val Asp Arg Tyr Trp Ala Ile Ser Arg
    130             135             140
Pro Phe Arg Tyr Lys Arg Lys Met Thr Gln Arg Met Ala Leu Val Met
145             150             155             160
Val Gly Leu Ala Trp Thr Leu Ser Ile Leu Ile Ser Phe Ile Pro Val
                165             170             175
Gln Leu Asn Trp His Arg Asp Gln Ala Ala Ser Trp Gly Gly Leu Asp
            180             185             190
Leu Pro Asn Asn Leu Ala Asn Trp Thr Pro Trp Glu Glu Asp Phe Trp
        195             200             205
Glu Pro Asp Val Asn Ala Glu Asn Cys Asp Ser Ser Leu Asn Arg Thr
    210             215             220
Tyr Ala Ile Ser Ser Ser Leu Ile Ser Phe Tyr Ile Pro Val Ala Ile
225             230             235             240
Met Ile Val Thr Tyr Thr Arg Ile Tyr Arg Ile Ala Gln Val Gln Ile
                245             250             255
Arg Arg Ile Ser Ser Leu Glu Arg Ala Ala Glu His Ala Gln Ser Cys
            260             265             270
Arg Ser Ser Ala Ala Cys Ala Pro Asp Thr Ser Leu Arg Ala Ser Ile
        275             280             285
Lys Lys Glu Thr Lys Val Leu Lys Thr Leu Ser Val Ile Met Gly Val
    290             295             300
Phe Val Cys Cys Trp Leu Pro Phe Phe Ile Leu Asn Cys Met Val Pro
305             310             315             320
Phe Cys Ser Gly His Pro Glu Gly Pro Pro Ala Gly Phe Pro Cys Val
                325             330             335
Ser Glu Thr Thr Phe Asp Val Phe Val Trp Phe Gly Trp Ala Asn Ser
            340             345             350
Ser Leu Asn Pro Val Ile Tyr Ala Phe Asn Ala Asp Phe Gln Lys Val
        355             360             365
Phe Ala Gln Leu Leu Gly Ser Ser His Phe Cys Ser Arg Thr Pro Val
    370             375             380
Glu Thr Val Asn Ile Ser Asn Glu Leu Ile Ser Tyr Asn Gln Asp Ile
385             390             395             400
Val Phe His Lys Glu Ile Ala Ala Ala Tyr Ile His Met Met Pro Asn
                405             410             415
Ala Val Thr Pro Gly Asn Arg Glu Val Asp Asn Asp Glu Glu Glu Gly
            420             425             430
Pro Phe Asp Arg Met Phe Gln Ile Tyr Gln Thr Ser Pro Asp Gly Asp
        435             440             445
Pro Val Ala Glu Ser Val Trp Glu Leu Asp Cys Glu Gly Glu Ile Ser
    450             455             460
Leu Asp Lys Ile Thr Pro Phe Thr Pro Asn Gly Phe His
465             470             475
```

( 2 ) INFORMATION FOR SEQ ID NO:3:

( i ) SEQUENCE CHARACTERISTICS:
    ( A ) LENGTH: 1683 base pairs
    ( B ) TYPE: nucleic acid
    ( C ) STRANDEDNESS: single ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
| CCCGGCGCAG | CTCATGGTGA | GCGCCTCTGG | GGCTCGAGGG | TCCCTTGGCT | GAGGGGGCGC | 60 |
| ATCCTCGGGG | TGCCCGATGG | GGCTGCCTGG | GGGTCGCAGG | GCTGAAGTTG | GGATCGCGCA | 120 |
| CAAACCGACC | CTGCAGTCCA | GCCCGAAATG | CTGCCGCCAA | GGAGCAACGG | CACCGCGTAC | 180 |
| CCGGGGCAGT | TAGCGCTATA | CCAGCAGCTG | GCGCAGGGGA | ACGCCGTGGG | GGCTCGGCG | 240 |
| GGGCACCGC | CACTGGGGCC | CGTGCAGGTG | GTCACCGCGT | GCCTGCTGAC | CCTGCTCATC | 300 |
| ATCTGGACCT | TGCTGGGCAA | CGTGCTGATG | TCCGCAGCCA | TCGTGCGGAG | CCGCCACCTG | 360 |
| CGCGCCAAGA | TGACCAACGT | CTTCATCGTG | TCTCTGGCTG | TGTCAGACCT | CTTCGTGGCG | 420 |
| CTGCTGGTCA | TGCCCTGGAA | GGCAGTCGCC | GAGGTGGCCG | GTTATTGGCC | CTTTGAAGCG | 480 |
| TTCTGCGACG | TCTGGGTGGC | CTTCGACATC | ATGTGCTCCA | CCGCCTCCAT | CCTGAACCTG | 540 |
| TGCGTCAGCA | GGTCATCAGC | GTGGCCCGCT | ACTGGGCCAT | CTCCAGGCCC | TTCCGCTACG | 600 |
| AGCGCAAGAT | GACCCAGCGC | ATGGCCTTGG | TCATGGTCGG | CCCGGCCTGG | ACCTTGTCCA | 660 |
| GCCTCATCTC | CTTCATTCCG | GTCCAGCTCA | ACTGGCACAG | GGACCAGGCG | GTCTCTTGAG | 720 |
| GTGGGCTGGA | CCTGCCAAAC | AACCTGGCCA | ACTGGACGCC | CTGGGAGGAG | GCCGTTTGGG | 780 |
| AGCCCGACGT | GAGGGCAGAG | AACTGTGACT | CCAGCCTGAA | TCGAACCTAC | GCCACTCCTT | 840 |
| CCTCGCTCAT | CAACTTCTAC | ATCCCCATGG | CCATCATGAT | CGTGACCTAC | ACGCGCATCT | 900 |
| ACCGCATCGC | CCAGGTGCAG | ATCTGCAGGA | TTTCCTCCTT | GGAGAGGGCC | GCAGAGCACG | 960 |
| TGCAGAGCTG | CCGGAGCAGC | GCAGGCTGCA | CGCCCGACAC | CAGCCTGCGG | TTTTCCATCA | 1020 |
| AGAAGGAGAC | CAAGGTTCTC | AAGCCCCTGT | CAGTGATCAT | GGGGGTCTTC | GTGTGTTGCT | 1080 |
| GGCTGCCCTT | CTTCATCCTT | AACTGCATGG | TCCCTTTCCG | CAGTGGACAC | CCCAAAGGCC | 1140 |
| CTCCGGCCGG | CTTCCCCTGC | GTCAGTGAGA | CCACATTCGA | TGTCTTCATC | TGGTTCTGCT | 1200 |
| GGGCCAACTC | CTCACTCAAC | CCAGTCACTA | TGCCTTCAAC | GCCGACTTCT | GGAAGGTGTT | 1260 |
| TGCCCAGCTG | CTGGGGTCGA | GCCACGTCTG | CTCCCGCACG | CCGGTGGAGA | CGGTGAACAT | 1320 |
| CAGCAATGAG | CTCATCTCCT | ACAACCAAGA | CATGGTCTTC | CACAAGGAAA | TCGCAGCTGC | 1380 |
| CTGCATCCAC | ATGATCGGCA | ACGCCGTTCC | CCCCGGGGAC | CAAGAGGTGG | ACAACGATGA | 1440 |
| GGAGGAGGAG | AGTCCTTTCG | ATCGCATGTC | CCAGATCTAT | CAGACATCCC | AGATGGTGA | 1500 |
| CCCTGTTGCA | GAGTCTGTCT | GAGAGCTGGA | CTGCGAGGGG | GAGATTTCTT | TAGACAAAAT | 1560 |
| AACGCCTTTC | ACCCCAAATG | GATTCCATTA | AACTGCATTA | AGAAACCCCC | TCATGGATCT | 1620 |
| GCATAACCGC | ACAGACACTG | ACAAGCACGC | ACACACGC | AAATACATGC | CTTTCCAGTA | 1680 |
| CTG | | | | | | 1683 |

( 2 ) INFORMATION FOR SEQ ID NO:4:

( i ) SEQUENCE CHARACTERISTICS:
        ( A ) LENGTH: 1681 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

| | | | | | |
|---|---|---|---|---|---|
| CCCGGCGCAC | CTCATGGTGA | GCGCCTCTGG | GGCTCGAGGG | TCCCTTGGCT | GAGGGGGCGC | 60 |
| ATCCTCGGGG | TGCCCGATGG | GGCTGCCTGG | GGGTCGCAGG | GCTGAAGTTG | GGATCGCGCA | 120 |

```
CAAACCGACC CTTCAGTCCA GCCCGAAATG CTGCCGCCAA GGAGCAACGG CACCGCGTAC    180
CCGGGGCAGT TAGCGCTGTA CCAGCAGCTG GCGCAGGGGA ATGCCGTGGG GGGCTCGGCG    240
GGGGCACCGC CACTGGGGCC CGTGCAGGTG GTCACCGCCT GCCTGCTGAC CCTACTCATC    300
ATCTGGACCT TGCTGGGCAA CGTGCTGGTG TCCGCAGCCA TCGTGCGGAG CCGCCACCTG    360
CGCGCCAAGA TGACCAACGT CTTCATCGTG TCTCTACCTG TGTCAGACCT CTTCGTGGCG    420
CTGCTGGTCA TGTCCTGGAA GGCAGTCGCC GAGGTGGCCG GTTACTGGCC CTTTGAAGCG    480
TTCTGCGACG TCTGGGTGGC CTTCGACATC ATGTGCTCCA CCGCCTCCAT CCTGAACCTG    540
TGCGTCAGCA GGTCATCAGC GTGGCCCGCT ACTGGGCCAT CTCCAGGCCC TTCCGTCACG    600
AGCGCAAGAT GACCCAGCGC ATGGCCTTGG TCATGGTCCG CCCGGCCTGG ACCTTGTCCA    660
GCCTCATCTC CTTCATTCCG GTCCAGCTCA ACTGGCACAG GGACCAGGCG GTCTCTTGAG    720
GTGGGCTGGA CCTGCCAAAC AACCTGGCCA ACTGGACGCC CTGGGAGGAG GCCGTTTGGG    780
AGCCCGACGT GAGGGCAGAG AACTGTGACT CCAGCCTGAA TCGAACCTAC GCCATCTCTT    840
CCTGCGTCAT CAGCTTCTAC ATCCCCATGG CCATCATGAT CGTGACCTAC ACGCGCATCT    900
ACCGCATCGC CCAGGTGCAG ATCCGCAGGA TTTCCTCCCT GGAGAGGGCC GCAGAGCACG    960
TGCAGAGCTG CCGGAGCAGC GCAGGCTGCG CGCCCGACAC CAGCCTGCGG TTTTCCATCA   1020
AGAAGGAGAC CGAGGTTCTC AAGACCCTGT CGGTGATCAT GGGGGTCTTC GTGTGTTGCT   1080
GGCTGCCCTT CTTCATCCTT AACTGCATGG TCCCTTTCTG CAGTGGACAC CCCAAAGCCT   1140
CCGGCCGGCT TCCCCTGCGT CAGTGAGACC ACATTCGACG TCTTCATCTG GTTCTGCTGG   1200
GCCAACTCCT CACTCAACCC AGTCACTATG CGTTCAACGC CGACTTCCGG AAGGTGTTTG   1260
CCCAGCTGCT GGGGTCGAGC CACGTCTGCT CCCGCACGCC GGTGGAGACG GTGAACATCA   1320
GCAATGAGCT CATCTCCTAC AACCAAGACA CGGTCTTCCA CAAGGAAATC GCAGCTGCCT   1380
ACATCCACAT GATGCCCAAC GCCGTTACCC CCGGGACCG GGAGGTGGAC AACGATGAGG    1440
AGGAGGAGAG TCCTTTCGAT CGCATGTCCC AGATCTATCA GACATCCCCA GATGGTGACC   1500
CTGTTGCAGA GTCTGTCTGA GAGCTGGACG GCGAGGGGA GATTTCTTTA GACAAAATAA    1560
CACCTTTCAC CCCAAATGGA TTCCATTAAA CTGCATTAAG AAACCCCCTC ATGGATCTGC   1620
ATAACCGCAC AGACACTGAC AAGCACGCAC ACACACGCAA ATACATGCCT TTCCAGTACT   1680
G                                                                  1681
```

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
CCGAATTCGC CTTCGACATC ATGTGC                                          26
```

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CCGGATCCGT CACGATCATG ATGGC 25

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CCGTCGACGA TCGCGCACAA ACCGAC 26

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CCGTCGACAG TACTGGAAAG GCATGTAT 28